(12) United States Patent
Shum et al.

(10) Patent No.: US 10,301,677 B2
(45) Date of Patent: May 28, 2019

(54) NORMALIZATION OF NUCLEIC ACID LIBRARIES

(71) Applicant: Cellular Research, Inc., Menlo Park, CA (US)

(72) Inventors: Eleen Shum, Menlo Park, CA (US); Glenn Fu, Menlo Park, CA (US); Craig Betts, Menlo Park, CA (US)

(73) Assignee: Cellular Research, Inc., San Jose, CA (US)

( * ) Notice: Subject to any disclaimer, the term of this patent is extended or adjusted under 35 U.S.C. 154(b) by 0 days.

(21) Appl. No.: 15/603,239

(22) Filed: May 23, 2017

(65) Prior Publication Data

US 2017/0342484 A1 Nov. 30, 2017

Related U.S. Application Data

(60) Provisional application No. 62/341,533, filed on May 25, 2016.

(51) Int. Cl.
| | | |
|---|---|---|
| C12Q 1/68 | (2018.01) | |
| C12Q 1/6874 | (2018.01) | |
| C12Q 1/6806 | (2018.01) | |
| G06F 19/20 | (2011.01) | |
| C12N 15/10 | (2006.01) | |

(52) U.S. Cl.
CPC ....... *C12Q 1/6874* (2013.01); *C12N 15/1065* (2013.01); *C12N 15/1093* (2013.01); *C12Q 1/6806* (2013.01); *G06F 19/20* (2013.01)

(58) Field of Classification Search
None
See application file for complete search history.

(56) References Cited

U.S. PATENT DOCUMENTS

| | | |
|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,773 A | 6/1998 | Li et al. |
| 5,763,175 A | 6/1998 | Brenner |
| 5,800,992 A | 9/1998 | Fodor et al. |
| 5,830,712 A | 11/1998 | Rampersad et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,235,475 B1 | 5/2001 | Brenner et al. |
| 6,268,152 B1 | 7/2001 | Fodor et al. |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |

(Continued)

FOREIGN PATENT DOCUMENTS

| | | |
|---|---|---|
| DE | 102008025656 | 12/2009 |
| EP | 0 799 897 | 10/1997 |

(Continued)

OTHER PUBLICATIONS

Bogdanova et al., Jan. 2008, Normalization of full-length enriched cDNA, Molecular Biosystems, 4(3):205-212.
Gu et al., 2016, Depletion of abundant sequences by hybridization (DSH): using Cas9 to remove unwanted high-abundance species in sequencing libraries and molecular counting applications, Genome Biology, 17:41, 13 pages.
Patanjali et al., Mar. 1991, Construction of a uniform-abundance (normalized) CNDA library, Proceedings of the National Academy of Sciences, 88(5):1943-1947.
Achim et al., May 2015, High-throughput spatial mapping of single-cell RNA-seq data to tissue of origin. Nature Biotechnology, 33(5):503-511.
Alkan et al., Oct. 2009, Personalized copy number and segmental duplication maps using next-generation sequencing. Nat Genet., 41(10):1061-1067.

(Continued)

*Primary Examiner* — James Martinell
(74) *Attorney, Agent, or Firm* — Knobbe, Martens, Olson & Bear, LLP

(57) ABSTRACT

This disclosure provides methods and compositions for removing one or more high abundance species from a plurality of nucleic acid molecules. In some embodiments, the methods and compositions can be used for normalizing nucleic acid libraries. In some embodiments, molecular labels are used in conjunction with the methods and compositions disclosed herein to improve sequencing efficiency.

20 Claims, 13 Drawing Sheets

(56) References Cited

U.S. PATENT DOCUMENTS

| | | |
|---|---|---|
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1 | 12/2006 | Sloge et al. |
| 7,393,665 B2 | 7/2008 | Brenner |
| 7,407,757 B2 * | 8/2008 | Brenner .................. C12P 19/34 435/6.12 |
| 7,424,368 B2 | 9/2008 | Huang et al. |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,228,229 B2 | 1/2016 | Olson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,567,645 B2 | 2/2017 | Fan et al. |
| 9,567,646 B2 | 2/2017 | Fan et al. |
| 9,582,877 B2 | 2/2017 | Fu et al. |
| 9,598,736 B2 | 3/2017 | Fan et al. |
| 9,637,799 B2 | 5/2017 | Fan et al. |
| 9,708,659 B2 | 7/2017 | Fodor et al. |
| 9,727,810 B2 | 8/2017 | Fodor et al. |
| 9,816,137 B2 | 11/2017 | Fodor et al. |
| 9,845,502 B2 | 12/2017 | Fodor et al. |
| 9,905,005 B2 | 2/2018 | Fu et al. |
| 2002/0072058 A1 | 6/2002 | Voelker et al. |
| 2002/0168665 A1 | 11/2002 | Okawa |
| 2003/0003490 A1 | 1/2003 | Fan et al. |
| 2003/0049616 A1 | 3/2003 | Brenner et al. |
| 2003/0082818 A1 | 5/2003 | Bahnson et al. |
| 2003/0104436 A1 | 6/2003 | Morris et al. |
| 2003/0175908 A1 | 9/2003 | Linnarson et al. |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0170373 A1 | 8/2005 | Monforte |
| 2005/0214825 A1 * | 9/2005 | Stuelpnagel ......... C12Q 1/6837 435/6.11 |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0041385 A1 | 2/2006 | Bauer et al. |
| 2006/0073506 A1 | 4/2006 | Christians et al. |
| 2006/0211030 A1 | 9/2006 | Brenner |
| 2006/0263709 A1 | 11/2006 | Matsumura et al. |
| 2006/0263789 A1 | 11/2006 | Kincaid |
| 2007/0020640 A1 | 1/2007 | Mccloskey et al. |
| 2007/0065823 A1 | 3/2007 | Dressman et al. |
| 2007/0117134 A1 | 5/2007 | Kou |
| 2007/0172873 A1 | 7/2007 | Brenner et al. |
| 2007/0178478 A1 | 8/2007 | Dhallan et al. |
| 2008/0070303 A1 | 3/2008 | West et al. |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0061513 A1 | 3/2009 | Andersson et al. |
| 2009/0105959 A1 | 4/2009 | Braverman et al. |
| 2009/0137407 A1 | 5/2009 | Church et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0298709 A1 | 12/2009 | Ma |
| 2010/0069250 A1 | 3/2010 | White, III et al. |
| 2010/0105049 A1 | 4/2010 | Ehrich et al. |
| 2010/0105886 A1 | 4/2010 | Woudenberg et al. |
| 2010/0120630 A1 | 5/2010 | Huang et al. |
| 2010/0255471 A1 | 10/2010 | Clarke |
| 2010/0291666 A1 | 11/2010 | Collier et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0040843 A1 | 2/2012 | Ducree et al. |
| 2012/0045844 A1 | 2/2012 | Rothberg et al. |
| 2012/0065081 A1 | 3/2012 | Chee |
| 2012/0071331 A1 | 3/2012 | Casbon et al. |
| 2012/0156675 A1 | 6/2012 | Lueerssen et al. |
| 2012/0163681 A1 | 6/2012 | Lohse |
| 2012/0173159 A1 | 7/2012 | Davey et al. |
| 2012/0190020 A1 | 7/2012 | Oliphant et al. |
| 2012/0220022 A1 | 8/2012 | Ehrlich et al. |
| 2012/0220494 A1 | 8/2012 | Samuels et al. |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0190206 A1 | 7/2013 | Leonard et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |

(56) References Cited

U.S. PATENT DOCUMENTS

| | | |
|---|---|---|
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0206547 A1 | 7/2014 | Wang et al. |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0066385 A1 | 3/2015 | Schnall-levin et al. |
| 2015/0113680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0225778 A1 | 8/2015 | Hindson et al. |
| 2015/0298091 A1 | 10/2015 | Weitz et al. |
| 2015/0307874 A1 | 10/2015 | Jaitin |
| 2015/0376609 A1 | 12/2015 | Hindson et al. |
| 2016/0026758 A1 | 1/2016 | Jabara et al. |
| 2016/0068889 A1 | 3/2016 | Gole et al. |
| 2016/0244828 A1 | 8/2016 | Mason |
| 2016/0257993 A1 | 9/2016 | Fu et al. |
| 2016/0289669 A1 | 10/2016 | Fan et al. |
| 2016/0289740 A1 | 10/2016 | Fu et al. |
| 2016/0312276 A1 | 10/2016 | Fu et al. |
| 2016/0320720 A1 | 11/2016 | Fan et al. |
| 2016/0326584 A1 | 11/2016 | Fodor et al. |
| 2016/0376583 A1 | 11/2016 | Murata et al. |
| 2016/0376648 A1 | 12/2016 | Fodor et al. |
| 2017/0073730 A1 | 3/2017 | Betts et al. |

FOREIGN PATENT DOCUMENTS

| | | |
|---|---|---|
| EP | 1 473 080 | 11/2004 |
| EP | 1 647 600 | 4/2006 |
| EP | 1 845 160 | 10/2007 |
| EP | 2 623 613 | 8/2013 |
| EP | 2 805 769 | 11/2014 |
| GB | 2293238 | 3/1996 |
| WO | WO 89/01050 | 2/1989 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO 02/056014 | 7/2002 |
| WO | WO 02/070684 | 9/2002 |
| WO | WO 04/017374 | 2/2004 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO 06/071776 | 7/2006 |
| WO | WO 06/102264 | 9/2006 |
| WO | WO 07/087310 | 8/2007 |
| WO | WO 07/087312 | 8/2007 |
| WO | WO 08/096318 | 8/2008 |
| WO | WO 09/148560 | 12/2009 |
| WO | WO 09/152928 | 12/2009 |
| WO | WO 10/117620 | 10/2010 |
| WO | WO 11/123246 | 10/2011 |
| WO | WO 11/143659 | 11/2011 |
| WO | WO 11/155833 | 12/2011 |
| WO | WO 12/038839 | 3/2012 |
| WO | WO 12/042374 | 4/2012 |
| WO | WO 12/047297 | 4/2012 |
| WO | WO 12/048341 | 4/2012 |
| WO | WO 12/083225 | 6/2012 |
| WO | WO 12/108864 | 8/2012 |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/162267 | 11/2012 |
| WO | WO 13/019075 | 2/2013 |
| WO | WO 13/117595 | 8/2013 |
| WO | WO 13/130674 | 9/2013 |
| WO | WO 13/173394 | 11/2013 |
| WO | WO 13/176767 | 11/2013 |
| WO | WO 13/177206 | 11/2013 |
| WO | WO 13/188672 | 12/2013 |
| WO | WO 13/188831 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO 14/028537 | 2/2014 |
| WO | WO 14/071361 | 5/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO 14/144495 | 9/2014 |
| WO | WO 14/201273 | 12/2014 |
| WO | WO 14/210353 | 12/2014 |
| WO | WO 15/002908 | 1/2015 |
| WO | WO 15/031691 | 3/2015 |
| WO | WO 15/035087 | 3/2015 |
| WO | WO 15/044428 | 4/2015 |
| WO | WO 15/047186 | 4/2015 |
| WO | WO 15/103339 | 7/2015 |
| WO | WO 15/117163 | 8/2015 |
| WO | WO 15/200869 | 12/2015 |

OTHER PUBLICATIONS

Anderson, Feb. 11, 2014, Study describes RNA sequencing applications for molecular indexing methods, genomeweb.com, 5 pp.
Ansorge, 2009, Next-generation DNA sequencing techniques. New Biotechnology, 25(4):195-203.
Atanur et al., Jun. 2010, The genome sequence of the spontaneously hypertensive rat: Analysis and functional significance, Genome Res., 20(6):791-803.
Audic et al., 1997, The Significance of Digital Gene Expression Profiles. Genome Research, 7:986-995.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http://bionumbers.hms.harvard.edu/KeyNumbers/aspx, 4 pp.
Bioscribe, Feb. 5, 2015, Massively parallel sequencing technology for single-cell gene expression published (press release), 3 pp.
Blainey, May 2013, The future is now: single-cell genomics of bacteria and archaea, FEMS Microbiol Rev., 37(3):407-427.
Bonaldo et al., Sep. 1996, Normalization and subtraction: two approaches to facilitate gene discovery. Genome Res., 6(9):791-806.
Braha et al., 2000, Simultaneous stochastic sensing of divalent metal ions. Nature Biotechnology, 18:1005-1007.

(56) References Cited

OTHER PUBLICATIONS

Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brisco et al., Jun. 25, 2012, Quantification of RNA integrity and its use for measurement of transcript number, Nucleic Acids Research, 40(18):e144.
Brodin et al., 2015, Challenges with using primer IDs to improve accuracy of next generation sequencing, 19(3):1-12.
Butkus, Feb. 6, 2014, Cellular research set to launch first gene expression platform using 'molecular indexing' technology, genomeweb.com, 5 pp.
Cai, Mar. 2013, Turning single cells in microarrays by super-resolution bar-coding, Brief Funct Genomics, 12(2):75-80.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castellarnau et al., Jan. 2015, Stochastic particle barcoding for single-cell tracking and multiparametric analysis, Small, 11(4):489-498.
Castle et al., Apr. 16, 2010, DNA copy number, including telomeres and mitochondria, assayed using next-generation sequencing. BMC Genomics, 11:244. doi: 10.1186/1471-2164-11-244.
Chamberlain et al., Dec. 9, 1968, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.
Church et al., 1988, Multiplex DNA sequencing. Science, 240:185-188.
Costello et al., Apr. 1, 2013, Discovery and characterization of artefactual mutations in deep coverage targeted capture sequencing data due to oxidative DNA damage during sample preparation. Nucleic Acids Res, 41(6):e67.
Cox. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Daines et al., Aug. 2009, High-throughput multiplex sequencing to discover copy number variants in *Drosophila*. Genetics, 182(4):935-941.
Dalerba et al., 2011, Single-cell dissection of transcriptional heterogeneity in human colon tumors, Nat Biotechnol., 29(12):1120-1127 and Supplementary Material.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.
De Saizieu et al., 1998, Bacterial transcript imaging by hybridization of total RNA to oligonucleotide arrays. Nature Biotechnology, 16:45-48.
Di Carlo et al., Dec. 1, 2008, Dynamic single-cell analysis for quantitative biology, Analytical Chemistry, 78(23):7918-7925.
Dirks et al., Oct. 26, 2004, Triggered amplification by hybridization chain reaction., Proc Nati Acad Sci U S A, 101(43), 15275-15278.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Feb. 6, 2015, Combinatorial labeling of single cells for gene expression cytometry. Science, 347(6222):1258367-8.
Fan et al., Jul. 19, 2012, Non-invasive prenatal measurement of the fetal genome. Nature, 487(7407):320-324.
Fan, Nov. 2010, Molecular counting: from noninvasive prenatal diagnostics to whole-genome haplotyping, doctoral dissertation, Stanford University, 185 pp.
Feldhaus et al., Jan. 15, 2000, Oligonucleotide-conjugated beads for transdominant genetic experiments, Nucleic Acids Res., 28(2):534-543.
Fox-Walsh et al., Oct. 2011, A multiplex RNA-seq strategy to profile poly(A+) RNA: application to analysis of transcription response and 3' end formation., Genomics, 98(4),266-271.
Fu et al., Mar. 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Gong et al., 2010, Massively parallel detection of gene expression in single cells using subnanolitre wells, Lab Chip, 10:2334-2337.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.
Gundry et al., Mar. 2012, Direct, genome-wide assessment of DNA mutations in single cells. Nucleic Acids Res., 40(5):2032-40.
Hacia et al., 1999, Determination of ancestral alleles for human single-nucleotide polymorphisms using high-density oligonucleotide arrays. Nature Genetics, 22:164-167.
Haff, 1994, Improved quantitative PCR using nested primers, PCR Methods and Applications, 3:332-337.
Hamady et al., Mar. 2008, Error-correcting barcoded primers for pyrosequencing hundreds of samples in multiplex. Nat Methods, 5(3):235-237.
Harrington et al., 2009, Cross-sectional characterization of HIV-1 env compartmentalization in cerebrospinal fluid over the full disease course, AIDS, 23(8) 907-915.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.

(56) References Cited

OTHER PUBLICATIONS

Hug et al., 2003, Measure of the number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Junker et al., May 21, 2015, Single-cell transcriptomics enters the age of mass production, Molecular Cell, 58:563-564.
Kanagawa, 2003, Bias and artifacts in multitemplate polymerase chain reactions (PCR), Journal of Bioscience and Bioengineering, 96(4):317-323.
Kebschull et al., Jul. 17, 2015, Sources of PCR-induced distortions in high-throughput sequencing data sets, Nucleic Acids Research, 15 pp.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kim et al., Jun. 8, 2007, Polony, multiplex analysis of gene expression (PMAGE) in mouse hypertrophic cardiomyopathy, Science, 316(5830):1481-1484.
Kinde et al., Jun. 7, 2011, Detection and quantification of rare mutations with massively parallel sequencing, Proc. Natl Acad Sci, 108(23):9530-0535.
Kivioja et al., Jan. 2012, Counting absolute numbers of molecules using unique molecular identifiers. Nature Methods, 9(1):72-76.
Klein et al., May 21, 2015, Droplet barcoding for single-cell transcriptomics applied to embryonic stem cells, Cell, 161:1187-1201.
Koboldt et al., Sep. 1, 2009, VarScan: variant detection in massively parallel sequencing of individual and pooled samples. Bioinformatics. 25(17):2283-2285.
Kolodziejczyk et al., May 21, 2015, The technology and biology of single-cell RNA sequencing, Molecular Cell, 58:610-620.
Konig et al., Jul. 2010, iCLIP reveals the function of hnRNAP particles in splicing at individual nucleotide resolution, Nature Structural & Molecular Biology, 17(7):909-916.
Kotake et al., 1996, A simple nested RT-PCR method for quantitation of the relative amounts of multiple cytokine mRNAs in small tissue samples, Journal of Immunological Methods, 199:193-203.
Kurimoto et al., Mar. 17, 2006, An improved single-cell cDNA amplification method for efficient high-density oligonucleotide microarray analysis, Nucleic Acids Res., 34(5):e42.
Lamble et al., Nov. 20, 2013, Improved workflows for high throughput library preparation using the transposome-based nextera system, BMC Biotechnology, 13(1):104.
Larson et al., Nov. 2009, A single molecule view of gene expression. Trends Cell Biol. 19(11):630-637.
Leamon et al., Nov. 2003, A massively parallel PicoTiterPlate based platform for discrete picoliter-scale polymerase chain reactions, Electrophoresis, 24(21):3769-3777.
Lee et al., 2010, Large-scale arrays of picolitre chambers for single-cell analysis of large cell populations, Lab Chip, 10:2952-2958.
Lee et al., Mar. 21, 2014, Highly multiplexed subcellular RNA sequencing in situ. Science. 343(6177):1360-1363.

Liu et al., Single-cell transcriptome sequencing: recent advances and remaining challenges, F1000Research 2016, 5(F1000 Faculty Rev):182, 9 pp.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods, 11(2):190-196.
Lucito et al., 1996, Representational Oligonucleotide Microarray Analysis: A High-Resolution Method to Detect Genome Copy Number Variation. Genome Research, 13: 2291-2305.
Maamar et al., 2007, Noise in Gene Expression Determines Cell Fate in *Bacillus subtilis*. Science, 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Makrigiorgos et al., Sep. 2002, A PCR-Based amplification method retaining quantities difference between two complex genomes. Nature Biotech, 20(9):936-939.
Marcus et al., 2006, Microfluidic single-cell mRNA isolation and analysis, Ana. Chem. 78:3084-3089.
Margulies et al., Sep. 15, 2005 Genome sequencing in microfabricated high-density picolitre reactors, Nature, 437:376-380.
Martinez et al., Jul. 2012, A microfluidic approach to encapsulate living cells in uniform alginate hydrogel microparticles, Macromol. Biosci, 12(7):946-951.
Mccloskey et al., Dec. 2007, Encoding PCR products with batch-stamps and barcodes. Biochem Genet. 45(11-12):761-767.
Medvedev et al., Nov. 2010, Detecting copy number variation with mated short reads. Genome Res. 20(11):1613-1622.
Mei et al., Mar. 22, 2010, Identification of recurrent regions of Copy-Number Variants across multiple individuals. BMC Bioinformatics. 11:147.
Merriam-Webster, definition of associate,: http://www.merriam-webster.com/dictionary/associate, accessed Apr. 5, 2016.
Miller et al., 2006, Directed evolution by in vitro compartmentalization, Nature Methods, 3:561-570.
Miner et al., 2004, Molecular barcodes detect redundancy and contamination in hairpin-bisulfate PCR, Nucleic Acids Research, 32(17):e135.
Mortazavi et al., 2008, Mapping and quantifying mammalian transcriptomes by RNA-Seq. Nat. Methods. 5:621-628.
Nadai et al., 2008, Protocol for nearly full-length sequencing of HIV-1 RNA from plasma, PLoS One, 3(1):e1420.
Nagai et al., 2001, Development of a microchamber array for picoleter PCR, Anal. Chem., 73:1043-1047.
Navin et al., 2015; The first five years of single-cell cancer genomics and beyond, Genome Research, 25(10):1499-1507.
Newell et al., Jan. 27, 2012, Cytometry by time-of-flight shows combinatorial cytokine expression and virus-specific cell niches within a continuum of CD8+ T cell phenotypes. Immunity. 36(1):142-152.
Novak et al., Jan. 20, 2011, Single-cell multiplex gene detection and sequencing with microfluidically generated agarose emulsions, Angew Chem Int Ed Engl., 50(2):390-395 redacted copy.
Ogino et al., Nov. 2002, Quantification of PCR bias caused by a single nucleotide polymorphism in SMN gene dosage analysis. J Mol Diagn. 4(4):185-190.
Parameswaran et al., 2007, A pyrosequencing-tailored nucleotide barcode design unveils opportunities for large-scale sample multiplexing. Nucleic Acids Res. 35(19):e130.
Park et al., May 2010, Discovery of common Asian copy number variants using integrated high-resolution array CGH and massively parallel DNA sequencing. Nat Genet. 42(5):400-405.
Peng et al., Mar. 11, 2016, Reducing amplification artifacts in high multiplex amplicon sequencing by using molecular barcodes, BMC

(56) References Cited

OTHER PUBLICATIONS

Genomics, retrieved from the Internet: url:http://bmcgenomics.biomedcentral.com/articles/0.1186/s12864-015-1806-8, 14 pp.
Pfaffl et al., Mar. 2004, Determination of stable housekeeping genes, differentially regulated target genes and sample integrity: BestKeeper—Excel-based tool using pair-wise correlations; Biotechnology Letters, 26(6):505-515.
Picelli et al., Jul. 30, 2014, Tn5 transposase and tagmentation procedures for massively scaled sequencing projects, Genome Research 24(12):2033-2040.
Pihlak et al., 2008, Rapid genome sequencing with short universal tiling probes, Nature Biotechnology, 26:676-684.
Pinkel et al., 2005, Comparative Genomic Hybridization. Annual Review of Genomics and Human Genetics. 6:331-354.
Pleasance et al., Jan. 14, 2010, A small-cell lung cancer genome with complex signatures of tobacco exposure. Nature. 463(7278):184-190.
Plessy et al., Feb. 2013, Population transcriptomics with single-cell resolution: a new field made possible by microfluidics: a technology for high throughput transcript counting and data-driven definition of cell types; Bioessays, 35(2):131-140.
Qiu et al., Oct. 2003, DNA sequence-based "bar codes" for tracking the origins of expressed sequence tags from a maize cDNA library constructed using multiple mRNA sources. Plant Physiol. 133(2):475-481.
Rajeevan et al., Oct. 2003, Global amplification of sense RNA: a novel method to replicate and archive mRNA for gene expression analysis, Genomics, 82(4):491-497.
Roche Diagnostics GmbH, 2006, Genome Sequencer 20 System: First to the Finish (product brochure), 40 pp.
Sasagawa et al., 2013, Quartz-Seq: a highly reproducible and sensitive single-cell RNA sequencing method, reveals non-genetic gene-expression heterogeneity. Genome Biology, 14:R31.
Sasuga et al., Dec. 2008, Single-cell chemical lysis method for analyses of intracellular molecules using an array of picoliter-scale microwells, Anal Chem, 80(23):9141-9149.
Satija et al., May 2015, Spatial reconstruction of single-cell gene expression data, Nature Biotechnology, 33(5):495-508.
Schmitt et al., Sep. 4, 2012, Detection of ultra-rare mutations by next-generation sequencing. Proc Natl Acad Sci U S A. 109(36):14508-14513.
Sebat et al., 2004, Large-Scale Copy Number Polymorphism in the Human Genome. Science, 305:525-528.
Shalek et al., Jun. 13, 2013, Single-cell transcriptomics reveals bimodality in expression and splicing in immune cells. Nature. 498(7453):236-240.
Shiroguchi et al., Jan. 24, 2012, Digital RNA sequencing minimizes sequence-dependent bias and amplification noise with optimized single-molecule barcodes, Proc Natl Acad Sci U S A. 109(4):1347-1352.
Shoemaker et al., 1996, Quantitative phenotypic analysis of yeast deletion mutants using a highly parallel molecular bar-coding strategy. Nature Genetics, 14:450-456.
Simpson et al., Feb. 15, 2010, Copy number variant detection in inbred strains from short read sequence data. Bioinformatics. 26(4):565-567.
Smith et al., 2010, Highly-multiplexed barcode sequencing: an efficient method for parallel analysis of pooled samples. Nucleic Acids Research, 38(13):e142.
Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.
Speicher et al., Oct. 2005, The new cytogenetics: blurring the boundaries with molecular biology, Nature Reviews Genetics, 6(10):782-792.
Stratagene 1998 Catalog, Gene Characterization Kits, p. 39.
Takahashi et al., Mar. 2006, Novel technique of quantitative nested real-time PCR assay for mycobacterium tuberculosis DNA, Journal of Clinical Microbiology, 44(3):1029-1039.
Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.
Taudien et al., Apr. 19, 2010, Haplotyping and copy number estimation of the highly polymorphic human beta-defensin locus on 8p23 by 454 amplicon sequencing. BMC Genomics. 11:252.
The Tibbs Times, UNC bioscience newsletter, Apr. 2010, 17 pp.
Tomaz et al., Aug. 2010, Differential methylation as a cause of allele dropout at the imprinted GNAS locus, Genet Test Mol Biomarkers. 14(4):455-460.
Treutlein et al., May 15, 2014, Reconstructing lineage hierarchies of the distal lung epithelium using single-cell RNA-seq. Nature. 509(7500):371-375.
Vandesompele et al., Jun. 18, 2002, Accurate normalization of real-time quantitative RT-PCR data by geometric averaging of multiple internal control genes, Genome Biology, 3(7).
Velculescu et al., 1995, Serial Analysis of Gene Expression. Science, 270:484-487.
Velculescu et al., 1997, Characterization of the Yeast Transcriptome. Cell, 88:243-251.
Vogelstein et al., 1999, Digital PCR. Proc. Natl. Acad. Sci., 96(16):9236-9241.
Walker et al., Jan. 1, 1992, Isothermal in vitro amplification of DNA by a restriction enzyme/DNA polymerase system. Proc Natl Acad Sci U S A., 89(1):392-396.
Walsh et al., Jul. 13, 2010, Detection of inherited mutations for breast and ovarian cancer using genomic capture and massively parallel sequencing. Proc Natl Acad Sci U S A. 107(28):12629-12633.
Wang et al., 2009, RNA-Seq: a revolutionary tool for transcriptomics. Nature Reviews Genetics, 10:57-63.
Wang et al., May 21, 2015, Advances and applications of single-cell sequencing technologies, Molecular Cell, 58(4):598-609.
Wang et al., Oct. 2010, iCLIP predicts the dual splicing effects of TIA-RNA interactions, PLoS Biol, 8(10):e1000530.
Warren et al., Nov. 21, 2006, Transcription factor profiling in individual hematopoietic progenitors by digital RT-PCR, PNAS, 103(47):17807-17812.
Weber et al., Sep. 15, 2003, A real-time polymerase chain reaction assay for quantification of allele ratios and correction of amplification bias. Anal Biochem. 320(2):252-258.
Weiner et al., Apr. 2008, Kits and their unique role in molecular biology: a brief retrospective, BioTechniques, 44:701-704.
White et al., Aug. 23, 2011, High-throughput microfluidic single-cell RT-qPCR, PNAS, 108(34):13999-14004.
Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nanogram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage. Genome Res. 19(9):1586-1592.
Zhang et al., Jun. 19, 2012, DNA-based hybridization chain reaction for amplified bioelectronic signal and ultrasensitive detection of proteins. Anal Chem., 84(12),5392-5399.
Zhang et al., Mar. 20, 2011, The impact of next-generation sequencing on genomics. J Genet Genomics. 38(3):95-109.

(56) References Cited

OTHER PUBLICATIONS

Zhao et al., 2005, Homozygous Deletions and Chromosome Amplifications in Human Lung Carcinomas Revealed by Single Nucleotide Polymorphism Array Analysis. Cancer Research, 65:5561-5570.
Zheng et al., Feb. 2016, Haplotyping germline and cancer genomes with high-throughput linked-read sequencing, Nature Biotechnology, 34(3):303-311.
Zhou et al., 2001, Counting alleles reveals a connection between chromosome 18q loss and vascular invasion. Nature Biotechnology, 19:78-81.
International Search Report and Written Opinion dated May 3, 2016 in PCT/US16/018354.
Office action dated Oct. 3, 2013 for U.S. Appl. No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office action dated Jul. 20, 2016 for U.S. Appl. No. 14/281,706.
Office Action dated Oct. 11, 2016 in U.S. Appl. No. 15/224,460.
Office Action dated May 8, 2017 in U.S. Appl. No. 15/224,460.
Office Action dated May 7, 2015 for U.S. Appl. No. 13/327,526.
Notice of allowance dated Jan. 21, 2016 for U.S. Appl. No. 13/327,526.
Office Action dated Jul. 28, 2017 in U.S. Appl. No. 14/975,441.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
International Search Report and Written Opinion dated Jun. 6, 2012 in PCT/US11/065291.
Office Action dated Feb. 17, 2017 in Canadian patent application No. 2,865,575.
Office Action dated Jun. 6, 2016 in Chinese patent application No. 201380022187.9.
Office Action dated Dec. 27, 2016 in Chinese patent application No. 201380022187.9.
Office Action dated Jul. 14, 2017 in Chinese patent application No. 201380022187.9.
European search report and search opinion dated Jul. 17, 2015 for European patent application No. 13755319.4.
Examination report dated Jul. 12, 2016 in European patent application No. 13755319.4.
Search and Examination Report dated Aug. 6, 2014 for GB patent application No. 1408829.8.
Search and Examination Report dated Jan. 27, 2016 in GB patent application No. 1408829.8.
Examination Report dated Jun. 8, 2016 in GB patent application No. 1408829.8.
Official Action dated Dec. 28, 2016 in Japanese patent application No. 2014-558975.
Restriction Requirement dated Mar. 15, 2016 in U.S. Appl. No. 14/381,488.
Office Action dated May 10, 2016 in U.S. Appl. No. 14/381,488.
Office Action dated Aug. 12, 2016 in U.S. Appl. No. 14/381,488.
Office Action dated Feb. 13, 2017 in U.S. Appl. No. 14/381,488.
Office Action dated Jun. 7, 2017 in U.S. Appl. No. 14/381,488.
Search Report and Written Opinion dated Mar. 1, 2016 in Singapore patent application No. 11201405274W.
Written Opinion dated May 26, 2017 in Singapore patent application No. 11201405274W.
International Search Report and Written Opinion dated Sep. 6, 2013 in PCT/US13/028103.
Extended European Search Report dated Dec. 15, 2015 in European patent application No. 13754428.4.
International search report and written opinion dated Aug. 16, 2013 for PCT/US2013/027891.
Office Action dated Apr. 11, 2016 in U.S. Appl. No. 14/472,363.
Restriction Requirement dated Mar. 17, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
Office action dated Aug. 17, 2016 for U.S. Appl. No. 14/800,526.
Office Action dated Oct. 25, 2016 in U.S. Appl. No. 14/872,337.
Office action dated Sep. 26, 2016 in U.S. Appl. No. 15/167,807.
Examination Report dated Apr. 10, 2017 in European patent application No. 14761937.3.
Search and Examination Report dated Aug. 26, 2015 in GB patent application No. 1511591.8.
Examination Report dated Feb. 19, 2016 in Great Britain patent application No. GB1511591.8.
Examination Report dated Jun. 15, 2016 in Great Britain patent application No. GB1511591.8.
Combined Search and Examination Report dated Feb. 21, 2017 in GB patent application No. 1609740.4.
International Search Report and Written Opinion dated Feb. 3, 2015 in PCT/US/14/053301.
Third Party Observation dated Jun. 14, 2018 in Japanese patent application No. 2016-537867.
Official Action dated Jul. 30, 2018 in Japanese patent application No. 2016-537867.
Office Action dated May 13, 2016 in U.S. Appl. No. 14/508,911.
Office Action dated Mar. 24, 2017 in U.S. Appl. No. 15/409,355.
International search report and written opinion dated Dec. 19, 2014 for PCT Application No. US2014/059542.
International Search Report and Written Opinion dated Jun. 20, 2016 in PCT/US16/14612.
Office Action dated Jan. 19, 2017 in U.S. Appl. No. 15/055,445.
International Search Report and Written Opinion dated Jun. 17, 2016 in PCT/US16/019962.
Written Opinion dated Jul. 5, 2016 in PCT/US16/019962.
Written Opinion dated Sep. 27, 2016 in PCT/US16/019962.
Invitation to Pay Additional Search Fees dated Jun. 2, 2016 in PCT/US16/019971.
International Search Report and Written Opinion dated Aug. 9, 2016 in PCT/US16/019971.
International Search Report and Written Opinion dated Jun. 9, 2016 in PCT/US16/022712.
International Search Report and Written Opinion dated Dec. 5, 2016 in PCT/US16/024783.
International Search Report and Written Opinion dated Sep. 28, 2016 in PCT/US16/028694.
International Search Report and Written Opinion dated Sep. 27, 2016 in PCT/US16/034473.
International Search Report and Written Opinion dated Jan. 31, 2017 in PCT/US16/050694.
International Search Report and Written Opinion dated Aug. 7, 2017 in PCT/US2017/034576.
International Search Report and Written Opinion dated Mar. 28, 2018 in patent application No. PCT/US2018/014385.
International search report and written opinion dated May 7, 2012 for PCT/IB2011/003160.
Notice of opposition dated Jul. 22, 2015 for European patent application No. 11810645.9.
Notice of opposition dated Jul. 9, 2015 for European patent application No. 11810645.9.

\* cited by examiner

NORMALIZATION OF NUCLEIC ACID LIBRARIES

RELATED APPLICATIONS

The present application claims priority under 35 U.S.C. § 119(e) to U.S. Provisional Application No. 62/341,533, filed on May 25, 2016, which is herein expressly incorporated by reference in its entirety.

BACKGROUND

The level of gene expression in a biological sample can vary greatly. For examples, it has been described that gene expression level follows 3 broad categories: 1) 'high expressers,' which are comprised of 5-10 genes that dominate ~20% of cellular mRNAs; 2) 'intermediate expressers' that are comprised of 50-200 genes that occupy 40-60% of cellular mRNAs; and 3) 'moderate expressers' that are comprised of 10,000-20,000 genes that occupy the rest of the cellular mRNA fraction. One challenge in molecular biology and molecular genetics is to be able to capture this highly dynamic gene expression profile efficiently and effectively in order to distinguish different cell types and phenotypes in the sample.

In recent years, next generation sequencing (NGS) has provided a high throughput method in assessing gene expression profiles. During library preparation for NGS, a sample with heterogeneous cDNA species is amplified by PCR to obtain adequate sample amount and to attach NGS-compatible adapters. The sequencing process captures the number of reads for each gene from the PCR-amplified library sample to interpret the gene expression level. However, since different genes are expressed at a large range of levels, PCR amplification can skew the native gene expression. For example, a gene has 1 molecule of cDNA would require 40 cycles of PCR to achieve the same representative amount as a gene with 1000 molecules of cDNA in 30 cycles. In a heterogeneous cDNA sample, PCR is usually performed in excess cycles to adequately amplify low expressers; in those scenarios, the native gene expression profile is usually skewed by the dominating high expresser PCR products. A method to correct for such bias in PCR product is Molecular Indexing; however, high expressers such as ribosomal protein mRNAs, mitochondrial mRNAs, or housekeeping genes often dominate the sequencing run with little contribution to the experimental interpretation, rendering the sequencing cost for Molecular Index counting to be expensive.

SUMMARY

Some embodiments disclosed herein provide methods of removing high abundance species from a plurality of nucleic acid molecules, comprising: hybridizing a plurality of first oligonucleotides comprising an affinity moiety with a first plurality of nucleic acid molecules, wherein the first plurality of nucleic acid molecules comprises at least one high abundance species; extending the plurality of oligonucleotides to generate a plurality of complementary strands of the first plurality of nucleic acid molecules comprising the affinity moiety; denaturing a plurality of double-stranded nucleic acid molecules comprising the plurality of complementary strands of the first plurality of nucleic acid molecules; partially reannealing the plurality of complementary strands of the first plurality of nucleic acid molecules; and removing the reannealed complementary strands of the first plurality of nucleic acid molecules by a capture molecule immobilized on one or more solid support to generate a second plurality of nucleic acid molecules, wherein the capture molecules specifically bind to the affinity moiety, whereby the at least one high abundance species is reduced in the second plurality of nucleic acid molecules. In some embodiments, the affinity moiety is a functional group selected from the group consisting of biotin, streptavidin, heparin, an aptamer, a click-chemistry moiety, digoxigenin, primary amine(s), carboxyl(s), hydroxyl(s), aldehyde(s), ketone(s), and any combination thereof. In some embodiments, the affinity moiety is biotin. In some embodiments, the capture molecule is streptavidin. In some embodiments, the methods further comprise synthesizing a second strand for each of the plurality of complementary strands of the first plurality of nucleic acid molecules to generate the plurality of double-stranded nucleic acid molecules comprising the plurality of complementary strands of the first plurality of nucleic acid molecules. In some embodiments, the synthesizing comprises hybridizing a plurality of second oligonucleotides to the plurality of complementary strands of the first plurality of nucleic acid molecules and extending the plurality of second oligonucleotide. In some embodiments, the plurality of first oligonucleotides or the plurality of second oligonucleotides comprises a universal primer binding site. In some embodiments, the methods further comprise amplifying the plurality of double-stranded nucleic acid molecules. In some embodiments, the first plurality of nucleic acid molecules comprises a plurality of high abundance species. In some embodiments, the plurality of high abundance species represents at least 50% of the first plurality of nucleic acid molecules. In some embodiments, the plurality of high abundance species represents at least 60% of the first plurality of nucleic acid molecules. In some embodiments, the plurality of high abundance species represents at least 70% of the first plurality of nucleic acid molecules. In some embodiments, at least 80% of the plurality of high abundance species is removed. In some embodiments, at least 90% of the plurality of high abundance species is removed. In some embodiments, at least 95% of the plurality of high abundance species is removed. In some embodiments, at least 99% of the plurality of high abundance species is removed. In some embodiments, the second plurality of nucleic acid molecules comprises the plurality of high abundance species. In some embodiments, the plurality of high abundance species in the second plurality of nucleic acid molecules represents less than 50% of the second plurality of nucleic acid molecules. In some embodiments, the plurality of high abundance species in the second plurality of nucleic acid molecules represents less than 40% of the second plurality of nucleic acid molecules. In some embodiments, the plurality of high abundance species in the second plurality of nucleic acid molecules represents less than 30% of the second plurality of nucleic acid molecules. In some embodiments, the first plurality of nucleic acid molecules comprises a plurality of low abundance species. In some embodiments, the plurality of low abundance species represents less than 10% of the first plurality of nucleic acid molecules. In some embodiments, the plurality of low abundance species represents less than 5% of the first plurality of nucleic acid molecules. In some embodiments, the plurality of low abundance species represents less than 1% of the first plurality of nucleic acid molecules. In some embodiments, the second plurality of nucleic acid molecules comprises the plurality of low abundance species. In some embodiments, the plurality of low abundance species in the second plurality of nucleic acid molecules represents at least 5% of the second plurality of nucleic acid molecules. In some embodiments, the plurality of low abundance species in the second plurality of nucleic acid molecules represents at least 10% of the second plurality of nucleic acid molecules. In some embodiments, the plurality of low abundance species in the second plurality of nucleic acid molecules represents at least 20% of the second plurality of nucleic acid molecules. In some embodiments, each of the first plurality of nucleic acid molecules or each of the second plurality of nucleic acid molecules comprises a stochastic barcode. In some embodiments, the methods further comprise sequencing the second plurality of nucleic acid molecules to generate a plurality of sequencing reads. In some embodiments, the sequencing reads for the plurality of high abundance species is less than 50% of the total sequencing reads. In some embodiments, the sequencing reads for the plurality of high abundance species is less than 40% of the total sequencing reads. In some embodiments, the sequencing reads for the plurality of high abundance species is less than 30% of the total sequencing reads. In some embodiments, the sequencing reads for the plurality of low abundance species is at least 5% of the total sequencing reads. In some embodiments, the sequencing reads for the plurality of low abundance species is at least 10% of the total sequencing reads. In some embodiments, the sequencing reads for the plurality of low abundance species is at least 20% of the total sequencing reads. In some embodiments, each of the plurality of sequencing reads comprises a molecular label. In some embodiments, the ratio of sequencing reads to molecular label for the plurality of high abundance species is less than 15. In some embodiments, the ratio of sequencing reads to molecular label for the plurality of high abundance species is less than 10. In some embodiments, the methods further comprise selectively depleting a high abundance species. In some embodiments, the selectively depleting comprises hybridizing a target-specific oligonucleotide that specifically binds to the high abundance species. In some embodiments, the selectively depleting comprises treating the first plurality of nucleic acid molecules with a Cas9 protein complexed with a guide oligonucleotide that specifically binds to the high abundance species.

Some embodiments disclosed herein provide methods of generating a normalized nucleic acid library, comprising: hybridizing a plurality of first oligonucleotides comprising an affinity moiety with a plurality of nucleic acid targets in a sample; extending the plurality of oligonucleotides to generate a plurality of complementary strands of the plurality of nucleic acid targets comprising the affinity moiety; denaturing a plurality of double-stranded nucleic acid molecules comprising the plurality of complementary strands of the plurality of nucleic acid targets; partially reannealing the plurality of complementary strands of the plurality of nucleic acid targets; and removing the reannealed complementary strands of the plurality of nucleic acid targets by a capture molecule immobilized on one or more solid support, wherein the capture molecules specifically bind to the affinity moiety, whereby a normalized nucleic acid library of the plurality of nucleic acid targets is generated. In some embodiments, the affinity moiety is a functional group selected from the group consisting of biotin, streptavidin, heparin, an aptamer, a click-chemistry moiety, digoxigenin, primary amine(s), carboxyl(s), hydroxyl(s), aldehyde(s), ketone(s), and any combination thereof. In some embodiments, the affinity moiety is a functional group selected from the group consisting of biotin, streptavidin, heparin, an aptamer, a click-chemistry moiety, digoxigenin, primary amine(s), carboxyl(s), hydroxyl(s), aldehyde(s), ketone(s), and any combination thereof. In some embodiments, the affinity moiety is biotin. In some embodiments, the capture molecule is streptavidin. In some embodiments, the methods further comprise synthesizing a second strand for each of the plurality of complementary strands of the plurality of nucleic acid targets to generate the plurality of double-stranded nucleic acid molecules comprising the plurality of complementary strands of the plurality of nucleic acid targets. In some embodiments, the synthesizing comprises hybridizing a plurality of second oligonucleotides to the plurality of complementary strands of the plurality of nucleic acid targets and extending the plurality of second oligonucleotide. In some embodiments, the plurality of first oligonucleotides or the plurality of second oligonucleotides comprises a universal primer binding site. In some embodiments, the methods further comprise amplifying the plurality of double-stranded nucleic acid molecules. In some embodiments, the plurality of nucleic acid targets comprises a plurality of low abundance nucleic acid targets. In some embodiments, the plurality of low abundance nucleic acid targets represents less than 10% of the plurality of nucleic acid targets. In some embodiments, the plurality of low abundance nucleic acid targets represents less than 5% of the plurality of nucleic acid targets. In some embodiments, the plurality of low abundance nucleic acid targets represents less than 1% of the plurality of nucleic acid targets. In some embodiments, the normalized nucleic acid library of the plurality of nucleic acid targets comprises the plurality of low abundance nucleic acid targets. In some embodiments, the plurality of low abundance nucleic acid targets in the normalized nucleic acid library represents at least 5% of the plurality of nucleic acid targets in the normalized nucleic acid library. In some embodiments, the plurality of low abundance nucleic acid targets in the normalized nucleic acid library represents at least 10% of the plurality of nucleic acid targets in the normalized nucleic acid library. In some embodiments, the plurality of low abundance nucleic acid targets in the normalized nucleic acid library represents at least 20% of the plurality of nucleic acid targets in the normalized nucleic acid library. In some embodiments, the plurality of nucleic acid targets comprises a plurality of high abundance nucleic acid targets. In some embodiments, the plurality of high abundance nucleic acid targets represents at least 50% of the plurality of nucleic acid target. In some embodiments, the plurality of high abundance nucleic acid targets represents at least 60% of the plurality of nucleic acid target. In some embodiments, the plurality of high abundance nucleic acid targets represents at least 70% of the plurality of nucleic acid target. In some embodiments, at least 80% of the plurality of high abundance nucleic acid targets is removed. In some embodiments, at least 90% of the plurality of high abundance nucleic acid targets is removed. In some embodiments, at least 95% of the plurality of high abundance nucleic acid targets is removed. In some embodiments, at least 99% of the plurality of high abundance nucleic acid targets is removed. In some embodiments, the normalized nucleic acid library of the plurality of nucleic acid targets comprises the plurality of high abundance nucleic acid targets. In some embodiments, the plurality of high abundance nucleic acid targets in the normalized nucleic acid library represents less than 50% of the plurality of nucleic acid targets in the normalized nucleic acid library. In some embodiments, the plurality of high abundance nucleic acid targets in the normalized nucleic acid library represents less than 40% of the plurality of nucleic acid targets in the normalized nucleic acid library. In some embodiments, the plurality of high abundance nucleic acid targets in the normalized nucleic acid library represents less than 30% of the plurality of nucleic acid targets in the normalized nucleic acid library. In some embodiments, each of the plurality of first oligonucleotides or each of the plurality of second oligonucleotides comprises a stochastic barcode. In some embodiments, the methods further comprise sequencing the normalized nucleic acid library to generate a plurality of sequencing reads. In some embodiments, the sequencing reads for the plurality of high abundance nucleic acid targets is less than 50% of the total sequencing reads. In some embodiments, the sequencing reads for the plurality of high abundance nucleic acid targets is less than 40% of the total sequencing reads. In some embodiments, the sequencing reads for the plurality of high abundance nucleic acid targets is less than 30% of the total sequencing reads. In some embodiments, the sequencing reads for the plurality of low abundance nucleic acid targets is at least 5% of the total sequencing reads. In some embodiments, the sequencing reads for the plurality of low abundance nucleic acid targets is at least 10% of the total sequencing reads. In some embodiments, the sequencing reads for the plurality of low abundance nucleic acid targets is at least 20% of the total sequencing reads. In some embodiments, each of the plurality of sequencing reads comprises a molecular label. In some embodiments, the ratio of sequencing reads to molecular label for the plurality of high abundance nucleic acid targets is less than 15. In some embodiments, the ratio of sequencing reads to molecular label for the plurality of high abundance nucleic acid targets is less than 10. In some embodiments, the plurality of nucleic acid targets comprises mRNA. In some embodiments, the plurality of nucleic acid targets comprises mitochondrial mRNA. In some embodiments, the plurality of nucleic acid targets comprises ribosomal protein mRNA. In some embodiments, the low abundance nucleic acid targets comprise 7,000 genes with the lowest number of transcripts. In some embodiments, the low abundance nucleic acid targets comprise 4,000 genes with the lowest number of transcripts. In some embodiments, the low abundance nucleic acid targets comprise 2,000 genes with the lowest number of transcripts. In some embodiments, the plurality of first oligonucleotides comprise target-specific primers. In some embodiments, the plurality of first oligonucleotides comprise non-target-specific primers. In some embodiments, the plurality of nucleic acid targets comprises cDNA. In some embodiments, the plurality of nucleic acid targets comprises genomic DNA. In some embodiments, the high abundance nucleic acid targets comprise short tandem repeat sequences. In some embodiments, the high abundance nucleic acid targets comprise telomeric sequences. In some embodiments, the high abundance nucleic acid targets comprise centrometic sequences. In some embodiments, the sample is a single cell. In some embodiments, the methods further comprise selectively depleting a high abundance species. In some embodiments, the selectively depleting comprises hybridizing a target-specific oligonucleotide that specifically binds to the high abundance species. In some embodiments, the selectively depleting comprises treating the first plurality of nucleic acid targets with a Cas9 protein complexed with a guide oligonucleotide that specifically binds to the high abundance species.

Some embodiments disclosed herein provide methods of generating a normalized nucleic acid library, comprising: hybridizing a plurality of first oligonucleotides comprising an affinity moiety with a plurality of nucleic acid targets in an unnormalized nucleic acid library; extending the plurality of oligonucleotides to generate a plurality of complementary strands of the plurality of nucleic acid targets comprising the affinity moiety; denaturing a plurality of double-stranded nucleic acid molecules comprising the plurality of complementary strands of the plurality of nucleic acid targets; partially reannealing the plurality of complementary strands of the plurality of nucleic acid targets; and removing the reannealed complementary strands of the plurality of nucleic acid targets, whereby a normalized nucleic acid library of the plurality of nucleic acid targets is generated. In some embodiments, the unnormalized nucleic acid library comprises one or more high abundance nucleic acid targets and one or more low abundance nucleic acid target. In some embodiments, the one or more high abundance nucleic acid targets represents at least 50% of the unnormalized nucleic acid library. In some embodiments, the one or more high abundance nucleic acid targets represents at least 60% of the unnormalized nucleic acid library. In some embodiments, the one or more high abundance nucleic acid targets represents at least 70% of the unnormalized nucleic acid library. In some embodiments, at least 80% of the plurality of high abundance nucleic acid targets is removed. In some embodiments, at least 90% of the plurality of high abundance nucleic acid targets is removed. In some embodiments, at least 95% of the plurality of high abundance nucleic acid targets is removed. In some embodiments, at least 99% of the plurality of high abundance nucleic acid targets is removed. In some embodiments, the one or more low abundance nucleic acid targets represents less than 10% of the unnormalized nucleic acid library. In some embodiments, the one or more low abundance nucleic acid targets represents less than 5% of the unnormalized nucleic acid library. In some embodiments, the one or more low abundance nucleic acid targets represents less than 1% of the unnormalized nucleic acid library. In some embodiments, the one or more low abundance nucleic acid targets represents at least 5% of the normalized nucleic acid library. In some embodiments, the one or more low abundance nucleic acid targets represents at least 10% of the normalized nucleic acid library. In some embodiments, the one or more low abundance nucleic acid targets represents at least 20% of the normalized nucleic acid library. In some embodiments, the one or more high abundance nucleic acid targets represents less than 50% of the normalized nucleic acid library. In some embodiments, the one or more high abundance nucleic acid targets represents less than 40% of the normalized nucleic acid library. In some embodiments, the one or more high abundance nucleic acid targets represents less than 30% of the normalized nucleic acid library. In some embodiments, the unnormalized nucleic acid library is a cDNA library. In some embodiments, the unnormalized nucleic acid library is a genomic library. In some embodiments, the unnormalized nucleic acid library is a single-cell library. In some embodiments, the methods further comprise selectively depleting a high abundance nucleic acid target. In some embodiments, the selectively depleting comprises hybridizing a target-specific oligonucleotide that specifically binds to the high abundance nucleic acid target. In some embodiments, the selectively depleting comprises treating the first plurality of nucleic acid targets with a Cas9 protein complexed with a guide oligonucleotide that specifically binds to the high abundance nucleic acid target.

DETAILED DESCRIPTION

Definitions

Figure 1A:
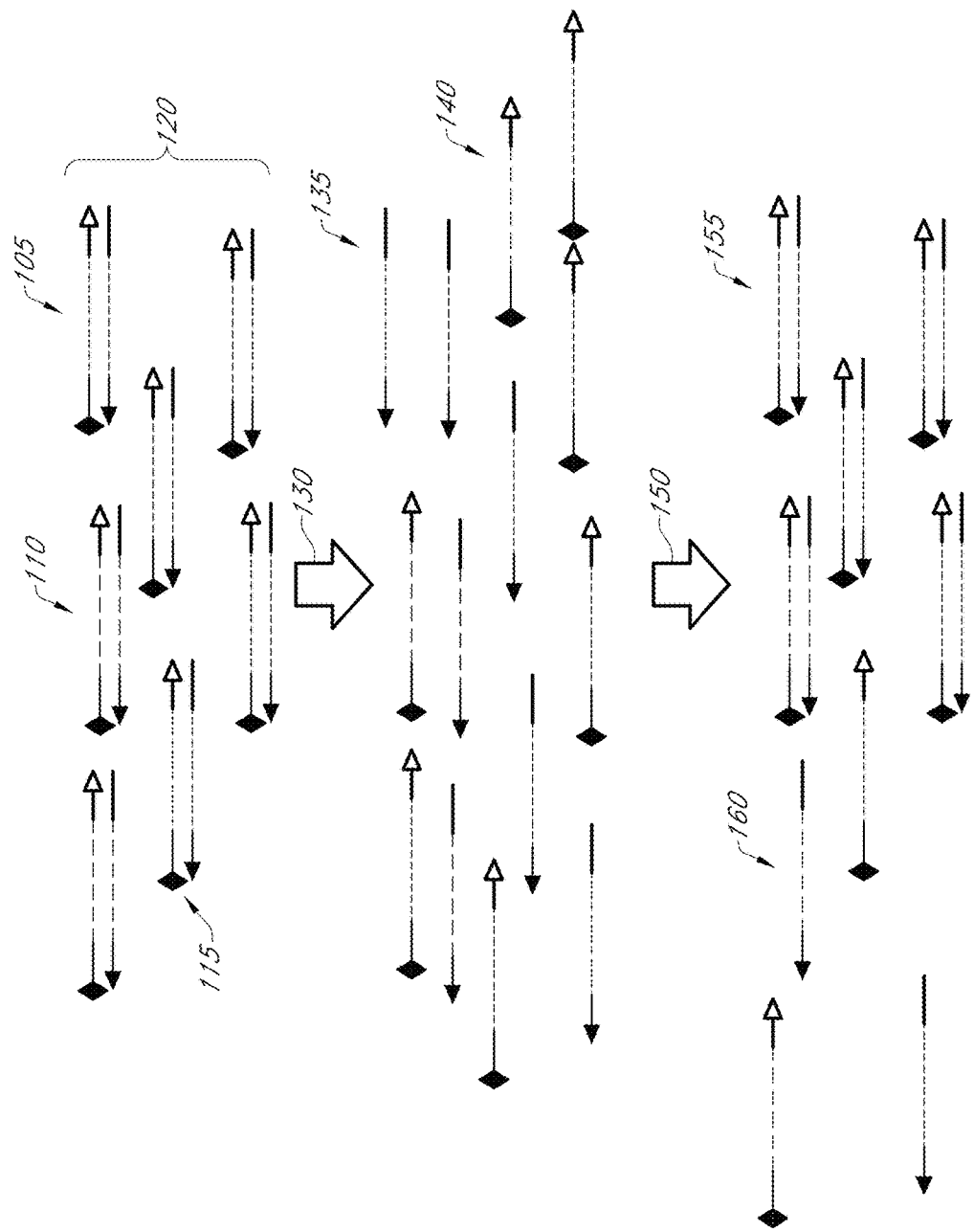
FIGS. 1A and 1B show a schematic illustration of exemplary library normalization by biotin immobilization.

Unless otherwise defined, all technical terms used herein have the same meaning as commonly understood by one of ordinary skill in the art in the field to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "attached", or "immobilized" to one another or to a common solid or semisolid surface. An association may refer to covalent or non-covalent means for attaching labels to solid or semi-solid supports such as beads. An association may comprise hybridization between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, a "nucleic acid" can generally refer to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backgone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or flurescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines.

Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone of the nucleic acid can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5, 4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (Hpyrido(3',':4,5)pyrrolo[2,3-d] pyrimidin-2-one).

As used herein, the term "sample" can refer to a composition comprising targets. Suitable samples for analysis by the disclosed methods, devices, and systems include cells, single cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be used interchangeably with the term "bead." As used herein, "solid support" and "substrate" can be used interchangeably.

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids. As used herein, "target" can be used interchangeably with "species".

The term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the Lactococc s lactis L1.LtrB intron reverse transcriptase, the Thermosynechococcus elongatus TeI4c intron reverse transcriptase, or the Geobacillus stearothermophilus intron reverse transcriptase. Other classes of reverse transcriptases can include many classes of non-retroviral reverse transcriptases (i.e., retrons, group II introns, and diversity-generating retroelements among others).

Methods of Removing High Abundance Species

Some embodiments disclosed herein provide methods of removing high abundance species from a plurality of nucleic acid molecules. In some embodiment, the methods disclosed herein can remove high abundance species from a plurality of nucleic acid molecules without significantly removing the low abundance species or the intermediate abundance species from the plurality of nucleic acid molecules. As used herein, "significantly removing" refers to removing at least 10%, at least 20%, at least 30%, at least 40%, at least 50% or more of a low abundance species or intermediate abundance species from the plurality of nucleic acid molecules.

In some embodiments, the methods disclosed herein can remove high abundance species and the intermediate abundance species from a plurality of nucleic acid molecules without significantly removing the low abundance species from the plurality of nucleic acid molecules.

As used herein, a "species" refers to the polynucleotides (for example, single-stranded polynucleotides) in the plurality of nucleic acid molecules that are the same or the complement of one another, or are capable of hybridize to one another, or are transcripts from the same genetic locus, or encode the same protein or fragment thereof, etc. In some embodiments, members of a species are at least 80%, at least 90%, at least 95%, at least 98%, at least 99%, or 100% homologous to one another, or complement thereof. In some embodiments, members of a species can hybridize to one another under high stringent hybridization conditions. In some embodiments, members of a species can hybridize to one another under moderate stringent hybridization conditions. In some embodiments, members of a species can hybridize to one another under low stringent hybridization conditions. In some embodiments, members of a species are transcripts from the same genetic locus and the transcripts can be of the same or different length. The species is, in some embodiments, cDNA or mRNA.

As used herein, a "high abundance species" refers to a species that is present in high amount in the plurality of nucleic acids, for example the species can represent at least 1%, 2%, 3%, 4%, 5%, 6%, 7%, 8%, 9%, 10%, 20%, 30%, 40%, 50%, or more of the plurality of nucleic acid molecules. In some embodiments, the plurality of nucleic acid molecules can comprise at least 1, at least 2, at least 3, at least 4, at least 5, at least 10, at least 20, at least 50, at least 100, at least 200, at least 500, at least 1,000, or more, high abundance species. In some embodiments, the total of all the high abundance species represent at least 10%, at least 20%, at least 30%, at least 40%, at least 50%, at least 60%, at least 70%, at least 80%, or more of the plurality of nucleic acid molecules. In some embodiments, high abundance species can comprise polynucleotides encoding one or more ribosomal proteins. In some embodiments, high abundance species can comprise polynucleotides encoding one or more mitochondrial proteins. In some embodiments, high abundance species can comprise polynucleotides encoding one or more housekeeping proteins.

As used herein, "intermediate abundance species" refers to a species that is present in an amount in the plurality of nucleic acid that is lower than at least one species in the plurality of nucleic acid and is higher than at least one other species in the plurality of nucleic acid. In some embodiments, an intermediate abundance species can represent about 10%, 5%, 4%, 3%, 2%, 1%, 0.1%, 0.01%, or a range between any two of the above values, of the plurality of nucleic acid molecules. In some embodiments, the plurality of nucleic acid molecules can comprise at least 1, at least 2, at least 3, at least 4, at least 5, at least 10, at least 20, at least 50, at least 100, at least 200, at least 500, at least 1,000, or more, intermediate abundance species. In some embodiments, the total of all the intermediate abundance species represent about 1%, about 2%, about 3%, about 4%, about 5%, about 10%, about 20%, about 30%, or a range between any two of the above values, of the plurality of nucleic acid molecules.

As used herein, "low abundance species" refers to a species that is present in low amount in the plurality of nucleic acids, for example the species can represent less than 1%, 0.1%, 0.01%, 0.001%, 0.0001%, or less of the plurality of nucleic acid molecules. In some embodiments, the plurality of nucleic acid molecules can comprise at least 1, at least 2, at least 3, at least 4, at least 5, at least 10, at least 20, at least 50, at least 100, at least 200, at least 500, at least 1,000, or more, low abundance species. In some embodiments, the total of all the low abundance species represent less than 20%, less than 10%, less than 5%, less than 4%, less than 3%, less than 2%, less than 1%, less than 0.1%, or less of the plurality of nucleic acid molecules. In some embodiments, low abundance species can comprise polynucleotides encoding one or more transcription factors. In some embodiments, high abundance species can comprise polynucleotides encoding one or more T cell receptors. In some embodiments, high abundance species can comprise polynucleotides encoding one or more antibodies.

In some embodiments, the methods and compositions disclosed herein can remove one or more high abundance species from the plurality of nucleic acid molecules. For example, the methods and compositions disclosed herein can remove at least 1, at least 2, at least 3, at least 4, at least 5, at least 10, at least 20, at least 50, at least 100, at least 200, at least 500, at least 1,000, or more, high abundance species. In some embodiments, the methods and compositions disclosed herein can remove at least 10%, at least 20%, at least 30%, at least 40%, at least 50%, at least 60%, at least 70%, at least 80%, at least 90%, at least 95%, or 100% of each of the one or more high abundance species from the plurality of nucleic acid molecules. In some embodiments, the methods and compositions disclosed herein can remove at least 10%, at least 20%, at least 30%, at least 40%, at least 50%, at least 60%, at least 70%, at least 80%, at least 90%, at least 95%, or 100% of at least one of the one or more high abundance species from the plurality of nucleic acid molecules. In some embodiments, the methods and compositions disclosed herein can remove at least 10%, at least 20%, at least 30%, at least 40%, at least 50%, at least 60%, at least 70%, at least 80%, at least 90%, at least 95%, or 100% of the total of high abundance species from the plurality of nucleic acid molecules.

In some embodiments, the methods and compositions disclosed herein can remove one or more high abundance species from the plurality of nucleic acid molecules without significantly removing the low abundance species or the intermediate abundance species from the plurality of nucleic acid molecules. In some embodiments, the methods and compositions disclosed herein can remove at least 10%, at least 20%, at least 30%, at least 40%, at least 50%, at least 60%, at least 70%, at least 80%, at least 90%, at least 95%, or 100% of each of the one or more high abundance species from the plurality of nucleic acid molecules without significantly removing the low abundance species or the intermediate abundance species from the plurality of nucleic acid molecules. In some embodiments, the methods and compositions disclosed herein can remove at least 10%, at least 20%, at least 30%, at least 40%, at least 50%, at least 60%, at least 70%, at least 80%, at least 90%, at least 95%, or 100% of the total of high abundance species from the plurality of nucleic acid molecules without significantly removing the low abundance species or the intermediate abundance species from the plurality of nucleic acid molecules. In some embodiments, the methods and compositions disclosed herein can remove one or more high abundance species from the plurality of nucleic acid molecules while keeping at least at least 50%, at least 60%, at least 70%, at least 80%, at least 90%, at least 95%, or 100% of each of the one or more low abundance species. In some embodiments, the methods and compositions disclosed herein can remove one or more high abundance species from the plurality of nucleic acid molecules while keeping at least at least 50%, at least 60%, at least 70%, at least 80%, at least 90%, at least 95%, or 100% of at least one of the one or more of low abundance species. In some embodiments, the methods and compositions disclosed herein can remove one or more high abundance species from the plurality of nucleic acid molecules while keeping at least at least 50%, at least 60%, at least 70%, at least 80%, at least 90%, at least 95%, or 100% of the total of low abundance species. In some embodiments, the methods and compositions disclosed herein can remove one or more high abundance species from the plurality of nucleic acid molecules while keeping at least at least 50%, at least 60%, at least 70%, at least 80%, at least 90%, at least 95%, or 100% of at least one of the one or more of intermediate abundance species. In some embodiments, the methods and compositions disclosed herein can remove one or more high abundance species from the plurality of nucleic acid molecules while keeping at least at least 50%, at least 60%, at least 70%, at least 80%, at least 90%, at least 95%, or 100% of the total of intermediate abundance species. In some embodiments, the methods and compositions disclosed herein can remove one or more high abundance species from the plurality of nucleic acid molecules while keeping at least 50%, at least 60%, at least 70%, at least 80%, at least 90%, at least 95%, or 100% of each of the intermediate abundance species from the plurality of nucleic acid molecules.

Plurality of Nucleic Acid Molecules

It would be appreciated by one of ordinary skill in the art that the plurality of nucleic acid molecules can comprise a variety of nucleic acid molecules. In some embodiments, the plurality of nucleic acid molecules can comprise, DNA molecules, RNA molecules, genomic DNA molecules, cDNA molecules, mRNA molecules, rRNA molecules, siRNA molecules, or a combination thereof, and can be double-stranded or single-stranded. In some embodiments, the plurality of nucleic acid molecules comprise at least 100, at least 1,000, at least 10,000, at least 20,000, at least 30,000, at least 40,000, at least 50,000, at least 100,000, at least 1,000,000, or more species. In some embodiments, the plurality of nucleic acid molecules can be from a sample, such as a single cell, or a plurality of cells. In some embodiments, the plurality of nucleic acid molecules can be pooled from a plurality of samples, such as a plurality of single cells.

In some embodiments, the plurality of nucleic acid molecules comprises an unnormalized nucleic acid library, a partially normalized nucleic acid library, or a nucleic acid library that has been normalized by other methods, such as a cDNA library, a genomic DNA library, or the like. In some embodiments, the plurality of nucleic acid molecules can comprise a pooled unnormalized nucleic acid library, such as a pooled unnormalized nucleic acid library constructed from a plurality of unnormalized nucleic acid libraries each representing a single cell. In some embodiments, the unnormalized nucleic acid library is a cDNA library. In some embodiments, the unnormalized nucleic acid library is a genomic library. In some embodiments, the unnormalized nucleic acid library is a single-cell nucleic acid library.

In some embodiments, the plurality of nucleic acid molecules can be subjected to amplification before removing the high abundance species. For example, the plurality of nucleic acid molecules can comprise an amplified nucleic acid library. In some embodiments, the plurality of nucleic acid molecules can comprise at least 2, at least 4, at least 8, at least 16, at least 100, at least 1,000 or more copies of each nucleic acid molecules.

Molecular Labels

It is contemplated that the methods and compositions disclosed herein can be used in conjunction of molecular labels, for example, nucleic acid molecules that comprise molecular labels. Accordingly, the species of nucleic acid molecules as disclosed herein can include polynucleotides in the plurality of nucleic acid molecules that are the same or the complement of one another, or are capable of hybridize to one another, or are transcripts from the same genetic locus, or encode the same protein or fragment thereof, etc., but that are associated with different molecular labels. It would be appreciated that molecular labels can be used to identify occurrences of a nucleic acid species, such as a high abundance species, a low abundance a species, and/or an intermediate abundance species. In some embodiments, a high abundance species can comprise nucleic acid molecules that comprise at least 100, at least 1,000, at least 10,000 or more different molecular labels. In some embodiments, a low abundance species can comprise nucleic acid molecules that comprise less than 100, less than 50, less than 20, less than 10, less than 5 or less different molecular labels. In some embodiments, an intermediate abundance species can comprise nucleic acid molecules that comprise about 10, about 20, about 50, about 100, or a range between any two of the above values, different molecular labels.

A molecular label may comprise a nucleic acid sequence that provides identifying information for the specific nucleic acid. A molecular label may comprise a nucleic acid sequence that provides a counter for the specific occurrence of the target nucleic acid. A molecular label may be at least about 1, 2, 3, 4, 5, 10, 15, 20, 25, 30, 35, 40, 45, 50 or more nucleotides in length. A molecular label may be at most about 300, 200, 100, 90, 80, 70, 60, 50, 40, 30, 20, 15, 12, 10, 9, 8, 7, 6, 5, 4 or fewer nucleotides in length.

It would be appreciated that in some embodiments, the methods and compositions disclosed herein may remove a high abundance species without significantly reducing the number of different molecular labels associated with the high abundance species. For example, the methods and compositions disclosed herein can remove a high abundance species while retaining at least at least 10%, at least 20%, at least 30%, at least 40%, at least 50%, at least 60%, at least 70%, at least 80%, at least 90%, at least 95%, or 100% of the different molecular labels associated with the high abundance species. In some embodiments, the methods and compositions disclosed herein can remove at least at least 10%, at least 20%, at least 30%, at least 40%, at least 50%, at least 60%, at least 70%, at least 80%, at least 90%, at least 95%, or at least 99% of a high abundance species while retaining at least at least 10%, at least 20%, at least 30%, at least 40%, at least 50%, at least 60%, at least 70%, at least 80%, at least 90%, at least 95%, or 100% of the different molecular labels associated with the high abundance species. In some embodiments, the removing of a high abundance species does not remove the number of different molecular labels associated with the high abundance species.

Accordingly, in some embodiments, the methods and compositions disclosed herein may remove a high abundance species without significantly reducing the number of different molecular labels associated with each of the intermediate or low abundance species. For example, the methods and compositions disclosed herein can remove a high abundance species while retaining at least at least 50%, at least 60%, at least 70%, at least 80%, at least 90%, at least 95%, or 100% of the different molecular labels associated with an intermediate or low abundance species. In some embodiments, the methods and compositions disclosed herein can remove at least at least 10%, at least 20%, at least 30%, at least 40%, at least 50%, at least 60%, at least 70%, at least 80%, at least 90%, at least 95%, or at least 99% of a high abundance species while retaining at least 50%, at least 60%, at least 70%, at least 80%, at least 90%, at least 95%, or 100% of the different molecular labels associated with an intermediate or low abundance species. In some embodiments, the removing of a high abundance species does not remove the number of different molecular labels associated with the high abundance species.

Affinity Moiety

In some embodiments, the methods disclosed herein comprise hybridizing a plurality of first oligonucleotides comprising an affinity moiety with the plurality of nuclei acid molecules. A variety of affinity moieties can be used for the methods and compositions disclosed herein. For example, an affinity moiety can be part of a binding pair. In some embodiments, the affinity moiety can be a functional group added to the oligonucleotides. In some embodiments, the affinity moiety can be biotin, streptavidin, heparin, an aptamer, a click-chemistry moiety, digoxigenin, primary amine(s), carboxyl(s), hydroxyl(s), aldehyde(s), ketone(s), or any combination thereof.

The affinity moieties as disclosed herein are capable of bind to a capture moiety such as a capture molecule. In some embodiments, the affinity moiety and capture molecule can be members of a binding pair, for example, biotin/streptavidin. The capture molecule can be immobilized on a solid support, such as a bead.

In some embodiments, the first oligonucleotides can be extended to generate a plurality of complementary strands of the plurality of nucleic acid targets comprising the affinity moiety. In some embodiments, a second strand can be synthesized using a primer that binds to a binding site on the complementary strands to produce double stranded nucleic acid molecules.

Remove High Abundance Species by Denaturation/Partial Reannealing

In some embodiments, removing of high abundance species can comprise denaturation followed by partial reannealing of the double stranded nucleic acid molecules, followed by removing the reannealed complementary strands of the plurality of nucleic acid targets by a capture molecule immobilized on one or more solid support, wherein the capture molecules specifically bind to the affinity moiety.

Denaturation can be performed by a variety of methods including heating the double stranded nucleic acid molecules, treating the double stranded nucleic acid molecules with organic solvents (e.g., DMS or formamide), changing the salt concentration of the double stranded nucleic acid molecules, and/or changing the pH of the double stranded nucleic acid molecules.

After denaturation, the single-stranded nucleic acid molecules can be partially reannealed. Partial reannealing can be performed by any method, for example, rapid cooling on ice, changing the salt concentration (e.g., reversing the salt concentration from the amount used in denaturation), and/or changing the pH (e.g., reversing the pH from the level used in denaturation), and the like.

It would be appreciated that the extent of reannealing can be adjusted according to the desired percentage of high abundance species to be removed, and/or the percentage of intermediate or low abundance species to be retained. Without being bound by any particular theory, it is believed that more abundant species (e.g., high abundance species) anneals faster than the species with lower abundance (e.g., intermediate and low abundance species) under the same anneal conditions. For example, by changing the temperature, salt concentration, pH, and/or duration of the reannealing step, the percentage of high abundance species to be removed, and/or the percentage of intermediate or low abundance species to be retained can be adjusted. In some embodiments, the temperature, salt concentration, pH, and/or duration of the reannealing step can be adjusted so that at least 10%, at least 20%, at least 30%, at least 40%, at least 50%, at least 60%, at least 70%, at least 80%, at least 90%, at least 95%, or at least 99% of a high abundance species reanneal. In some embodiments, the temperature, salt concentration, pH, and/or duration of the reannealing step can be adjusted so that at least 10%, at least 20%, at least 30%, at least 40%, at least 50%, at least 60%, at least 70%, at least 80%, at least 90%, at least 95%, or 100% of the intermediate or low abundance species remain single-stranded.

In some embodiments, the molecular labels associated with the high abundance species, intermediate or low abundance species can be used as an indicator for the adjustment of the reannealing conditions. For example, the temperature, salt concentration, pH, and/or duration of the reannealing step can be adjusted so that at least 10%, at least 20%, at least 30%, at least 40%, at least 50%, at least 60%, at least 70%, at least 80%, at least 90%, at least 95%, or 100% of the different molecular labels associated with one or more high abundance species are removed. In some embodiments, the temperature, salt concentration, pH, and/or duration of the reannealing step can be adjusted so that at least 50%, at least 60%, at least 70%, at least 80%, at least 90%, at least 95%, or 100% of the different molecular labels associated with one or more intermediate or low abundance species are retained.

Selective Depletion of High Abundance Species

In some embodiments, the methods disclosed herein comprise selective depletion of one or more high abundance species using target specific oligonucleotides comprising an affinity moiety. For example, the high abundance species can be removed by hybridizing an oligonucleotide that specifically binds to a high abundance species comprising an affinity moiety, followed by removing the high abundance species using a capture molecule immobilized on a solid support, wherein the capture molecule specifically binds to the affinity moiety. Exemplary high abundance species can comprise nucleic acid molecules that encode ribosomal proteins, mitochondrial proteins, housekeeping proteins, etc.

In some embodiments, Cas9 can be used to remove a high abundance species as described in Gu et al. Genome Biology (2016) 17:41, hereby incorporated by reference in its entirety for discussion of Cas nucleases-based removal of high abundance species.

Sequencing

In some embodiments, the normalized libraries disclosed herein may be used for sequencing. In some embodiments, the normalized libraries disclosed herein may be amplified prior to sequencing. Any suitable sequencing method known in the art can be used, preferably high-throughput approaches. For example, cyclic array sequencing using platforms such as Roche 454, Illumina Solexa, ABI-SOLiD, ION Torrent, Complete Genomics, Pacific Bioscience, Helicos, or the Polonator platform, may also be utilized. Sequencing may comprise MiSeq sequencing. Sequencing may comprise HiSeq sequencing.

It would be appreciated the normalized libraries can increase the efficiency of sequencing, by increasing the sequencing reads for intermediate or low abundance species in the normalized library, and/or decreasing the sequencing reads for high abundance species in the normalized library.

In some embodiments, after removing the high abundance species using the methods described herein, the sequencing reads for the plurality of high abundance nucleic acid targets is less than 50%, less than 40%, less than 30%, less than 20%, less than 10%, less than 5%, or less, of the total sequencing reads. In some embodiments, the sequencing reads for the plurality of high abundance nucleic acid targets is less than 40% of the total sequencing reads. In some embodiments, the sequencing reads for the plurality of high abundance nucleic acid targets is less than 30% of the total sequencing reads. In some embodiments, the sequencing reads for the plurality of high abundance nucleic acid targets is less than 20% of the total sequencing reads. In some embodiments, the sequencing reads for the plurality of high abundance nucleic acid targets is less than 10% of the total sequencing reads. The methods described herein for removing high abundance species can also improve the sequencing reads for intermediate and/or low abundance nucleic acid targets in a plurality of nucleic acids (e.g., a nucleic acid library). For example, the sequencing reads for the plurality of intermediate abundance nucleic acid targets can be at least 30%, at least 20%, at least 10%, at least 5%, of the total sequencing reads. In some embodiments, the sequencing reads for the plurality of low abundance nucleic acid targets can be at least 50%, at least 40%, at least 30%, at least 20%, at least 10%, at least 5%, at least 4%, at least 3%, at least 2%, at least 1%, of the total sequencing reads. In some embodiments, the sequencing reads for the plurality of low abundance nucleic acid targets is at least 5% of the total sequencing reads. In some embodiments, the sequencing reads for the plurality of low abundance nucleic acid targets is at least 10% of the total sequencing reads. In some embodiments, the sequencing reads for the plurality of low abundance nucleic acid targets is at least 20% of the total sequencing reads. In some embodiments, the sequencing reads for the plurality of low abundance nucleic acid targets is at least 30% of the total sequencing reads. In some embodiments, the sequencing reads for the plurality of low abundance nucleic acid targets is at least 40% of the total sequencing reads. In some embodiments, the sequencing reads for the plurality of low abundance nucleic acid targets is at least 50% of the total sequencing reads.

The methods and compositions disclosed herein can improve the sequencing efficiency of the normalized library by decreasing the sequencing reads:molecular label ratio of a high abundance species and/or increasing the sequencing reads:molecular label ratio of a low or intermediate abundance species. In some embodiments, the ratio of sequencing reads to molecular label for the plurality of high abundance species is less than 15, less than 10, less than 9, less than 8, less than 7, less than 6, less than 5, less than 4, less than 3, less than 2, less than 1. In some embodiments, the ratio of sequencing reads to molecular label for a high abundance species is less than 15, less than 10, less than 9, less than 8, less than 7, less than 6, less than 5, less than 4, less than 3, less than 2, less than 1. In some embodiments, the ratio of sequencing reads to molecular label for the plurality of low abundance species is at least 1, at least 2, at least 3, at least 4, at least 5, at least 6, at least 7, at least 8, at least 9, at least 10, or more. In some embodiments, the ratio of sequencing reads to molecular label for a low abundance species is at least 1, at least 2, at least 3, at least 4, at least 5, at least 6, at least 7, at least 8, at least 9, at least 10, or more. In some embodiments, the ratio of sequencing reads to molecular label for the plurality of intermediate abundance species is at least 1, at least 2, at least 3, at least 4, at least 5, at least 6, at least 7, at least 8, at least 9, at least 10, or more. In some embodiments, the ratio of sequencing reads to molecular label for an intermediate abundance species is at least 1, at least 2, at least 3, at least 4, at least 5, at least 6, at least 7, at least 8, at least 9, at least 10, or more.

Methods for Library Normalization

Figure 1B:
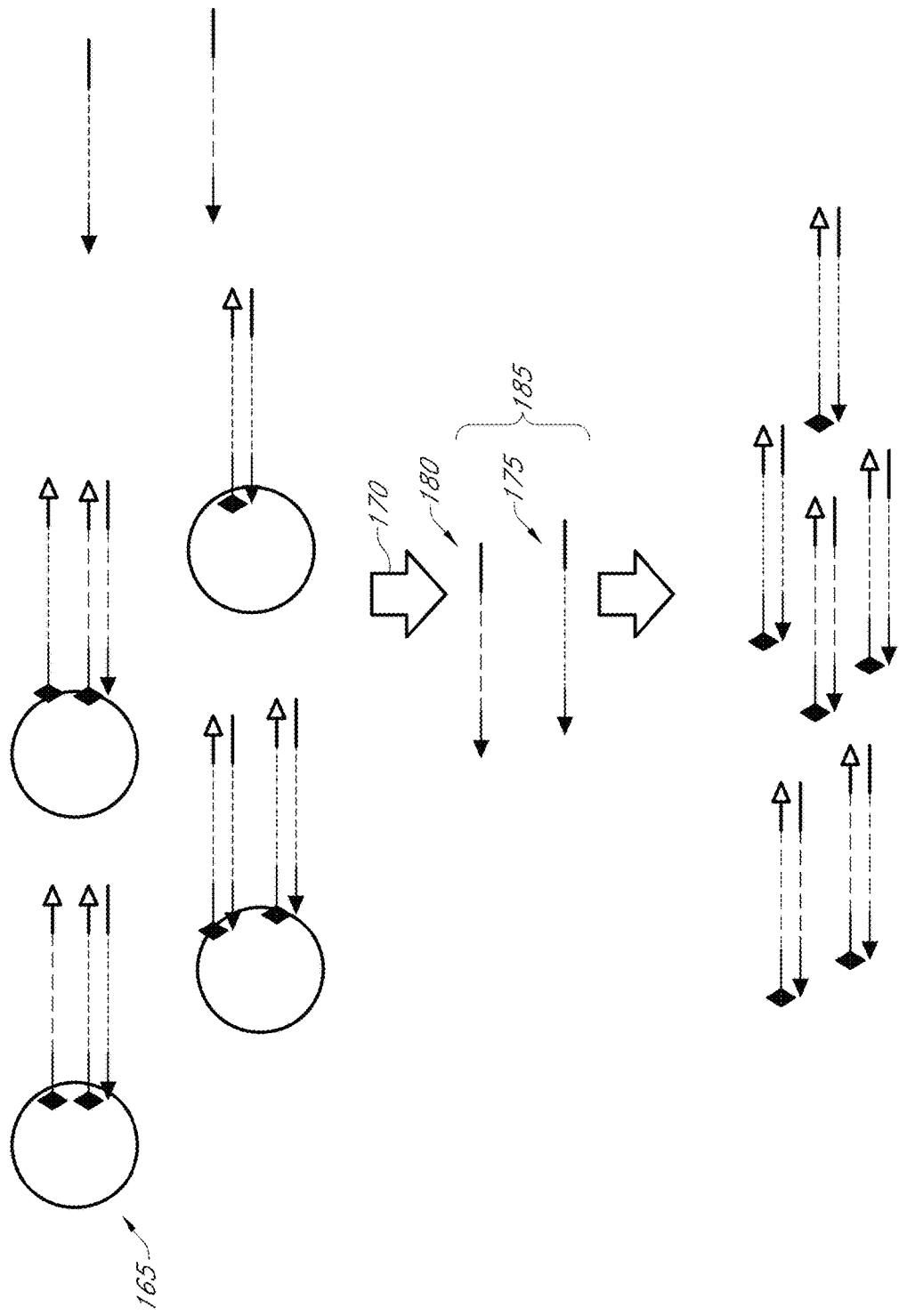

Methods and compositions described herein address the challenges of physical and enzymatic separation of ssDNA and dsDNA fractions during library normalization. As shown in FIG. 1, an unnormalized library contains a high abundance species 105 and a low abundance species 110. During initial library preparation, the library, or a fraction of the library, is asymmetrically labeled on one end with an affinity capture moiety 115 (such as biotin, etc.). The labeled double stranded nucleic acid molecules 120 are denatured 130 to generate single-stranded nucleic acid molecules including a high abundance species 135 and a low abundance species 140. The single-stranded nucleic acid molecules are partially reannealed 150 to form double-stranded molecules of the high abundance species 155 whereas the low abundance species remain single-stranded 160. After denaturation and partial reannealing, all of the labeled strands are captured on a support matrix 165, such as paramagnetic streptavidin beads, and the bound and unbound fractions are separated 170. Highly abundant sequences will have predominantly rehybridized, and both strands will be removed in the bound fraction. However, low abundance sequences will not have reannealed, so the complement of the labeled strand will be present in the unbound fraction. The unbound fraction including single-stranded high abundance species 175 and single-stranded low abundance species 180 would represent a normalized library 185, and could either be used directly or further amplified for downstream applications.

Library normalization strategies can be based on one of two principles. The first is hybridizing the library to another set of nucleic acids where the sequences are uniformly represented, such as the genomic DNA from the source organism, and retaining the hybridized fraction. The other approach relies on the concentration dependence of solution hybridization. When a set of dsDNA molecules are denatured, they will rehybridize at a rate proportional to the square of their original concentrations, as represented by the following equation:

$$\frac{\partial C}{\partial t} = kC^2$$

Wherein k=association constant, and C=concentration of a particular DNA species. Integration and plugging in ssDNA and ddDNA concentration:

$$[dsDNA] = \frac{[ssDNA]}{1 + [ssDNA]kt}$$

Without experimentally verifying what k constant is with our library and annealing condition, a k value that was presented in the literature (using optimal conditions) was used:

$$k = \frac{1}{5 \times 10^4 \times \sqrt{\text{length}}}$$

Where length is according to WTA Bioanalyzer, or N1 amplicon length.

Researcher exploit this property for library normalization by denaturing a mixture and only allowing it to partially reanneal; proportionally, much more of the high concentration species will have rehybridized to dsDNA while less abundant species will still be predominantly single stranded. The dsDNA and ssDNA are then separated by physical or enzymatic means. Physical separation typically requires prohibitively large amounts of starting material, and the nuclease most typically used is of variable quality purified from a non-recombinant source and is prone to digesting ssDNA in regions of local secondary structure.

Computer modeling of the cost-reducing effect and rare-transcript identification effect was performed by normalization on existing targeted and WTA sequencing experiments on the Precise and Resolve platforms.

EXAMPLES

Some aspects of the embodiments discussed above are disclosed in further detail in the following examples, which are not in any way intended to limit the scope of the present disclosure.

Example 1: Simulated from 'ES32 TCR Panel' Sequencing Results

Figure 2:
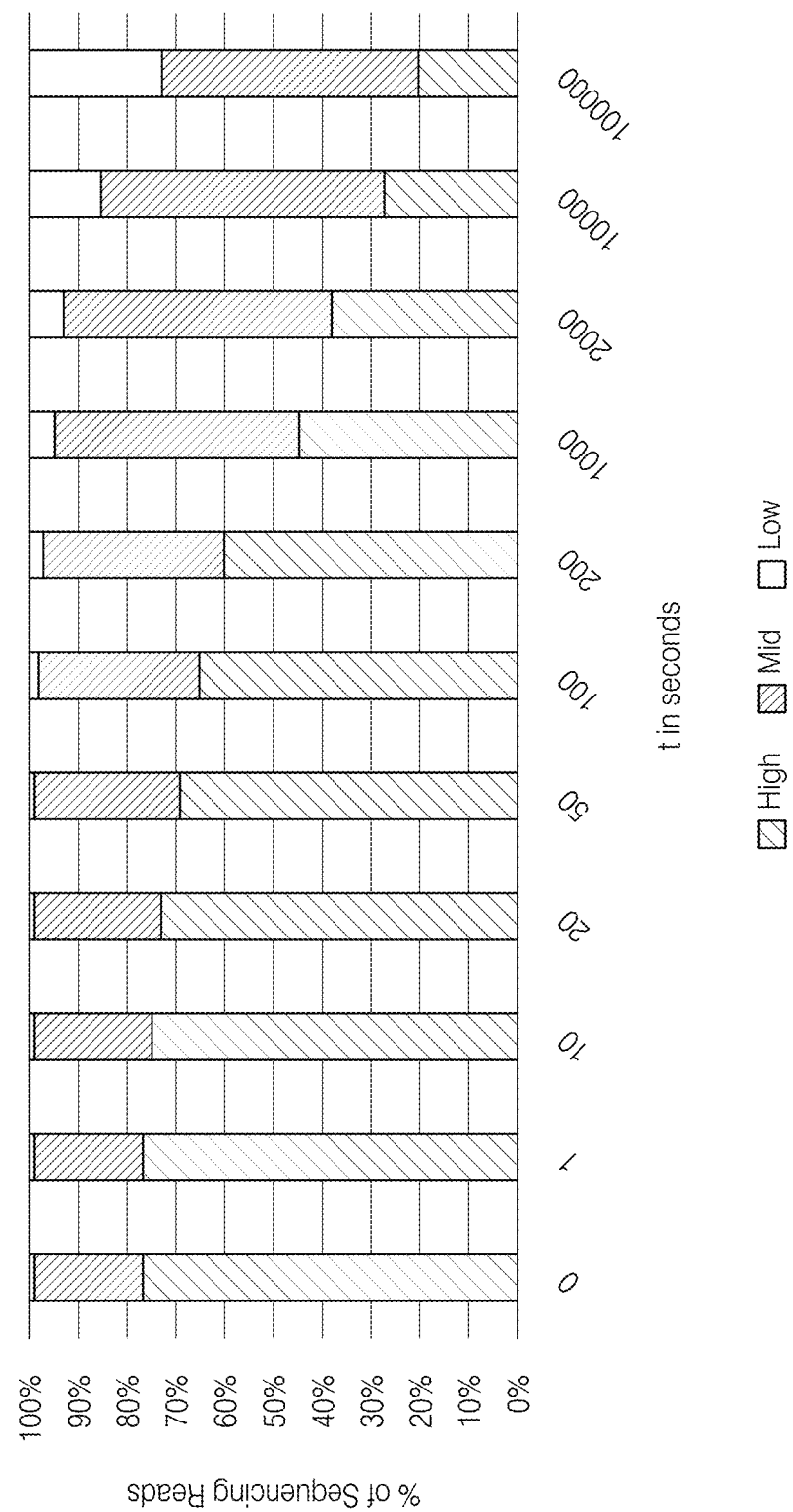
FIG. 2 shows simulated normalization results on sequencing reads using sequencing results from expression data of targeted TCR genes.
Figure 3:
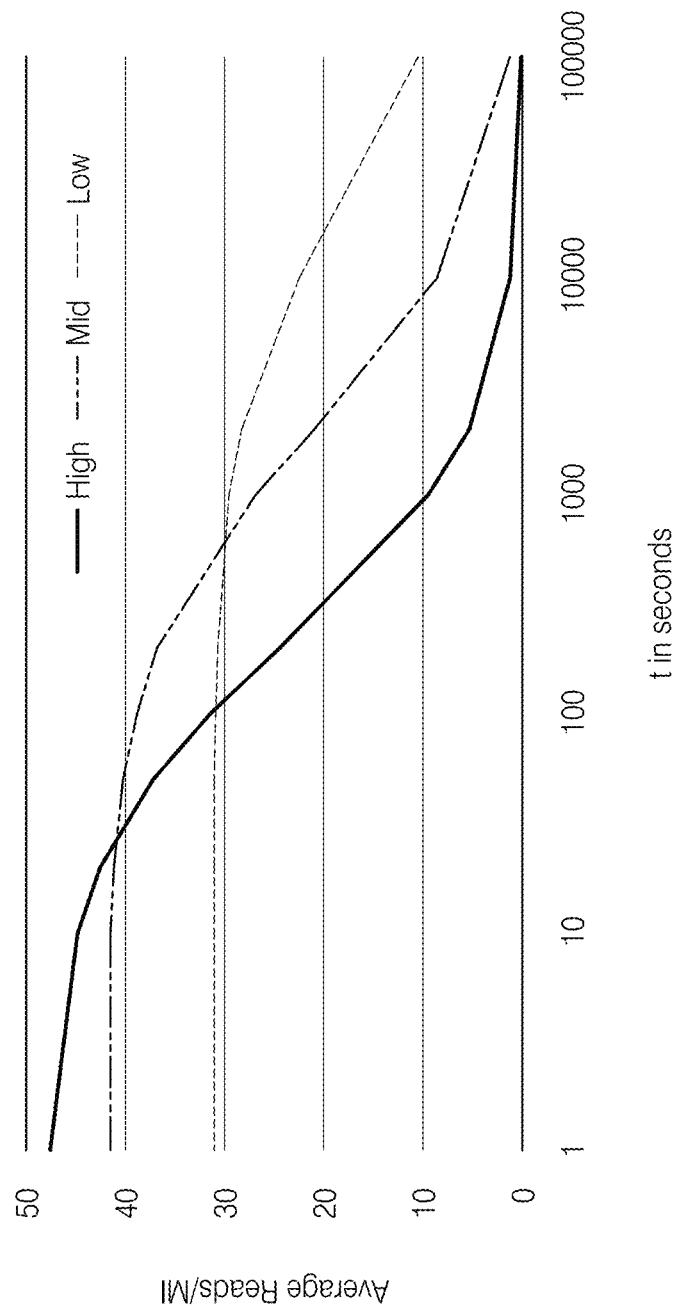
FIG. 3 shows simulated normalization results on average sequencing reads per MI using sequencing results from expression data of targeted TCR genes.

FIGS. 2-3 show computer simulated normalization results using ES32 TCR panel sequencing reads, which indicate % reads dedicated for low expressers or rare transcripts can be increased 100%+, potentially allowing higher sensitivity and precision in rare transcript counting.

With a smaller dynamic range in read ratio between high expressers and low expressers, targeted panel design can allow for high dynamic range transcripts.

The simulation results indicate normalization can reduce sequencing depth of high expressers and not the low expressers, yet retain the molecular label counting in over-sequenced libraries.

Example 2: Simulated from 'CBRepro' Sequencing Results

Figure 4:
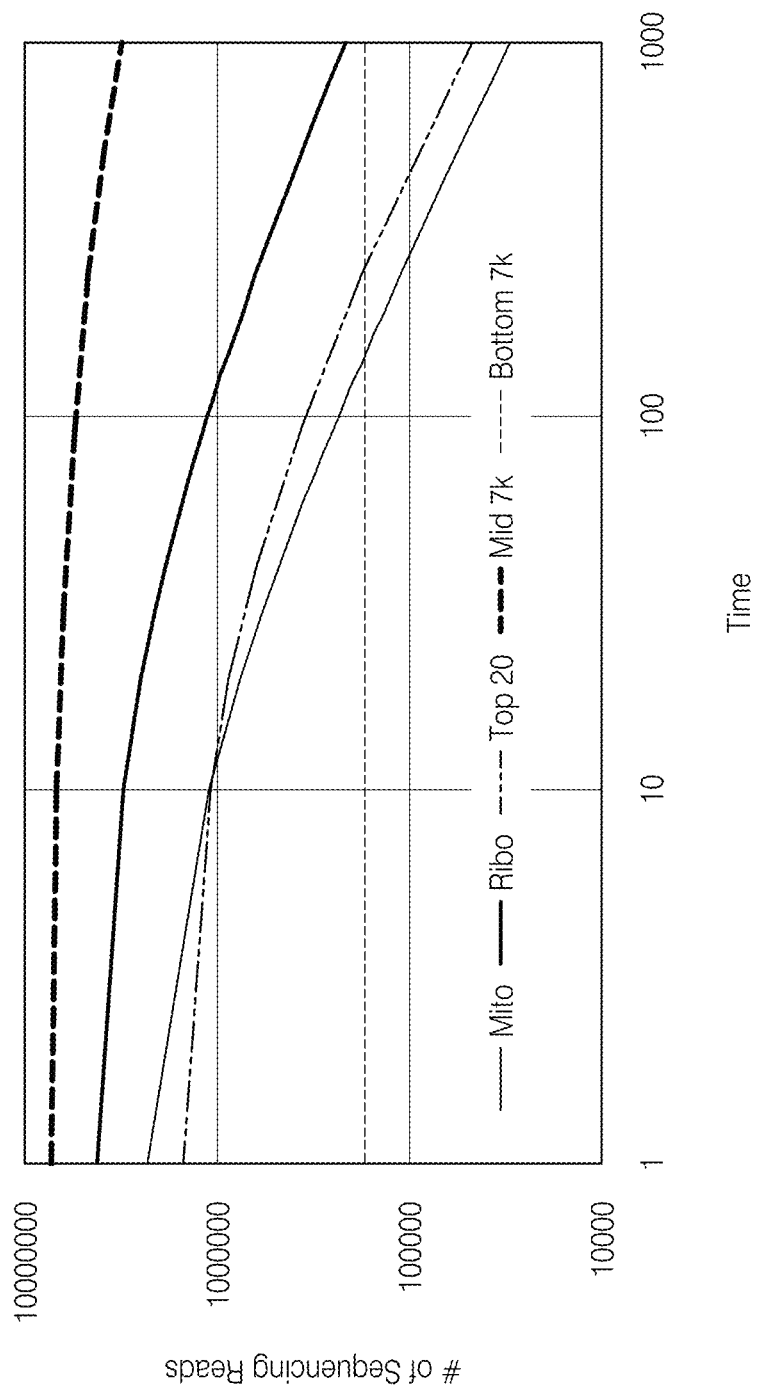
FIG. 4 shows simulated normalization results on sequencing reads using sequencing results from whole transcriptome amplification data.
Figure 5:
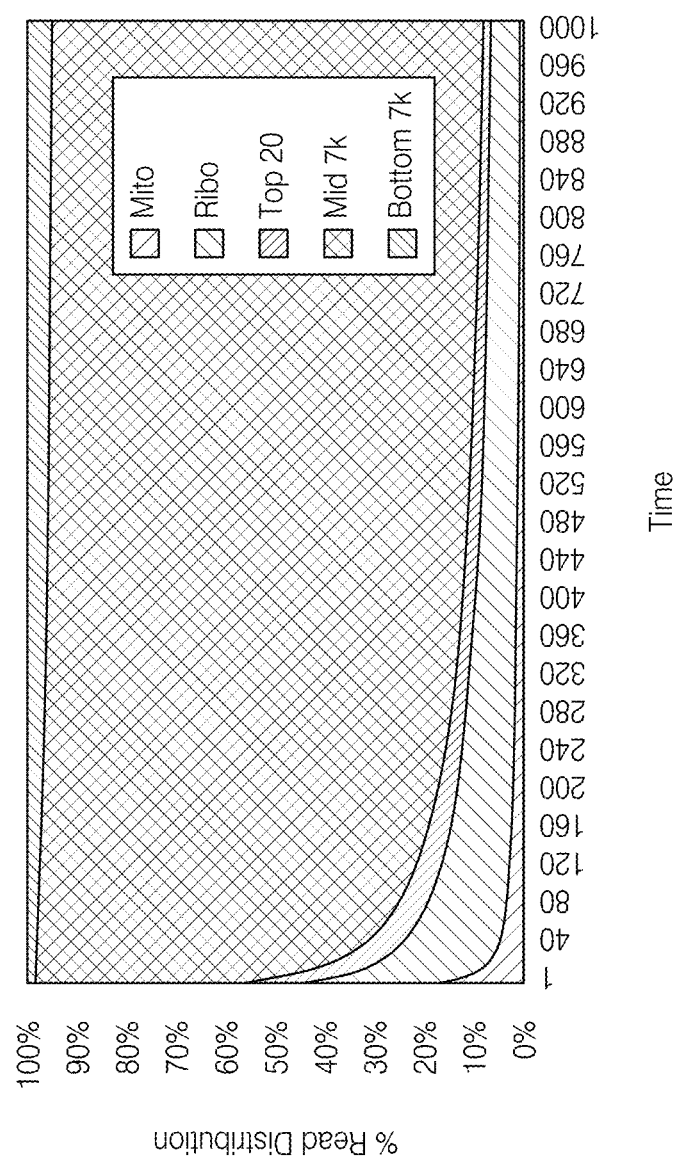
FIG. 5 shows simulated normalization results on sequencing read distribution using sequencing results from whole transcriptome amplification data.
Figure 6:
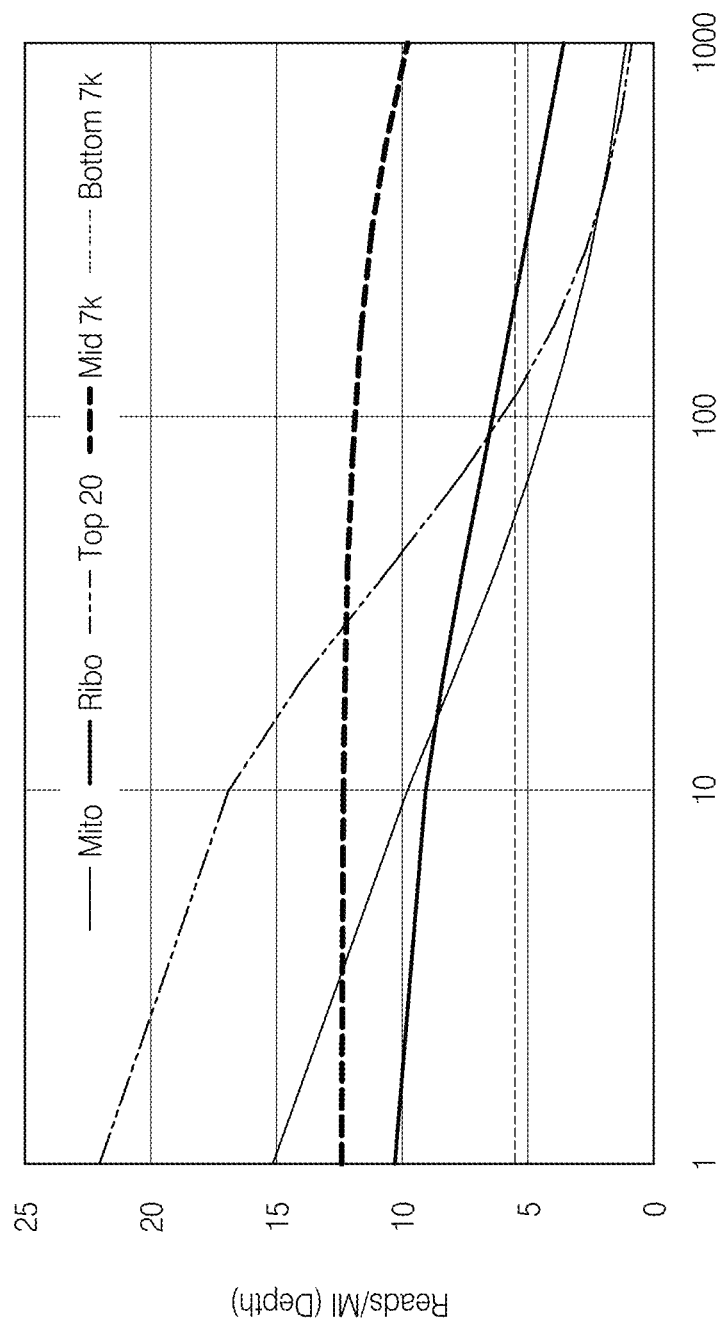
FIG. 6 shows simulated normalization results on sequencing reads per MI using sequencing results from whole transcriptome amplification data.

FIGS. 4-6 show computer simulated normalization results using CBRepro sequencing reads, which indicate normalization can reduce sequencing cost by at least 25% for the same output data by removing high expressers such as mitochondrial RNA and ribosomal protein RNA.

FIG. 6 shows sequencing depth primarily affects highly abundant transcripts.

Figure 7:
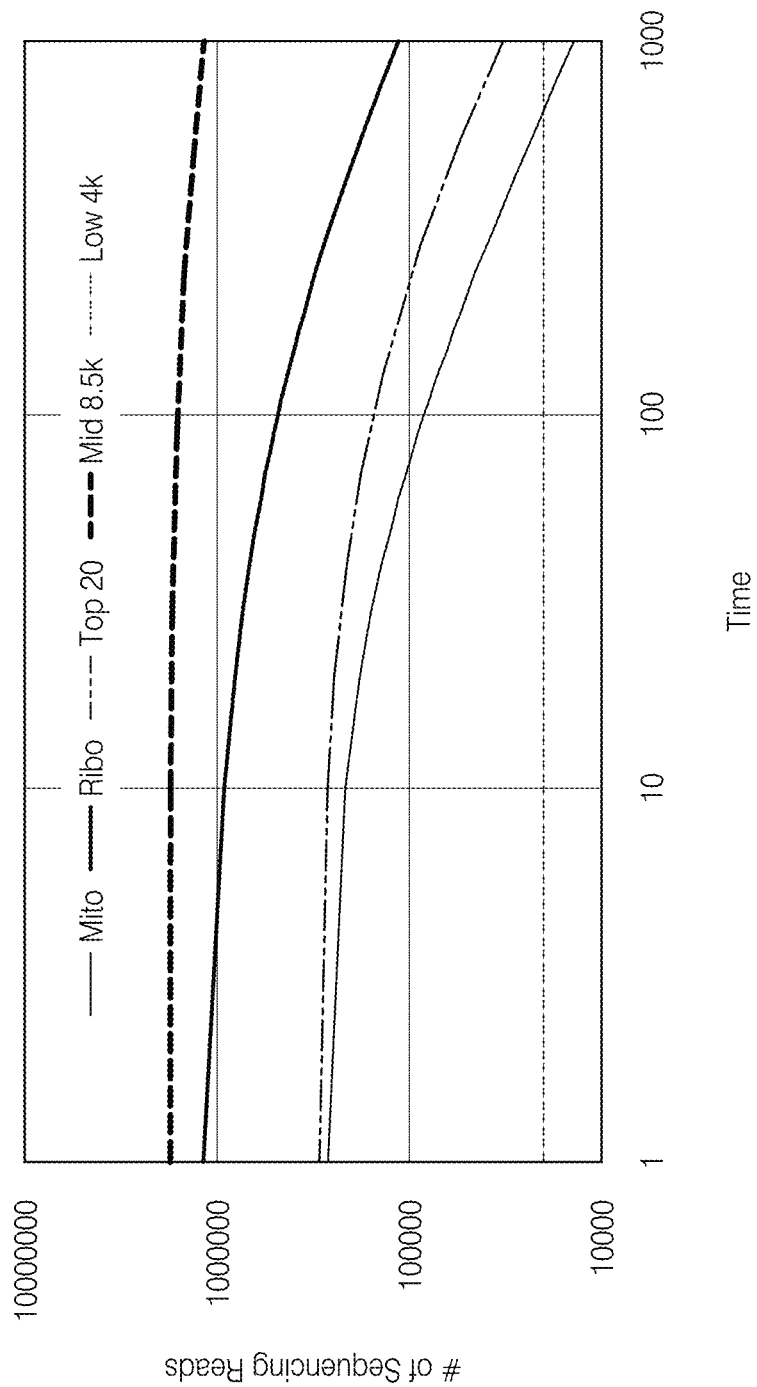
FIG. 7 shows simulated normalization results on sequencing reads using shallow sequencing results from single T cell whole transcriptome amplification data.
Figure 8:
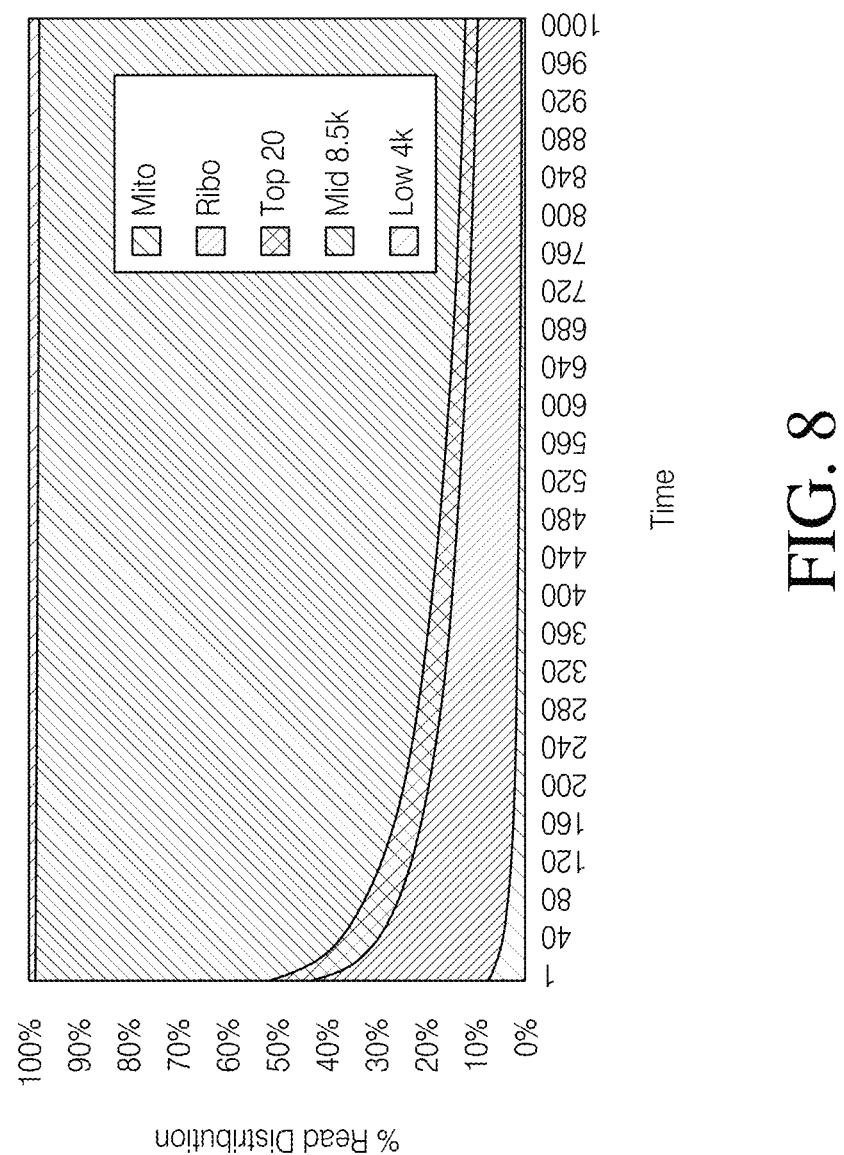
FIG. 8 shows simulated normalization results on sequencing read distribution using shallow sequencing results from single T cell whole transcriptome amplification data.
Figure 9:
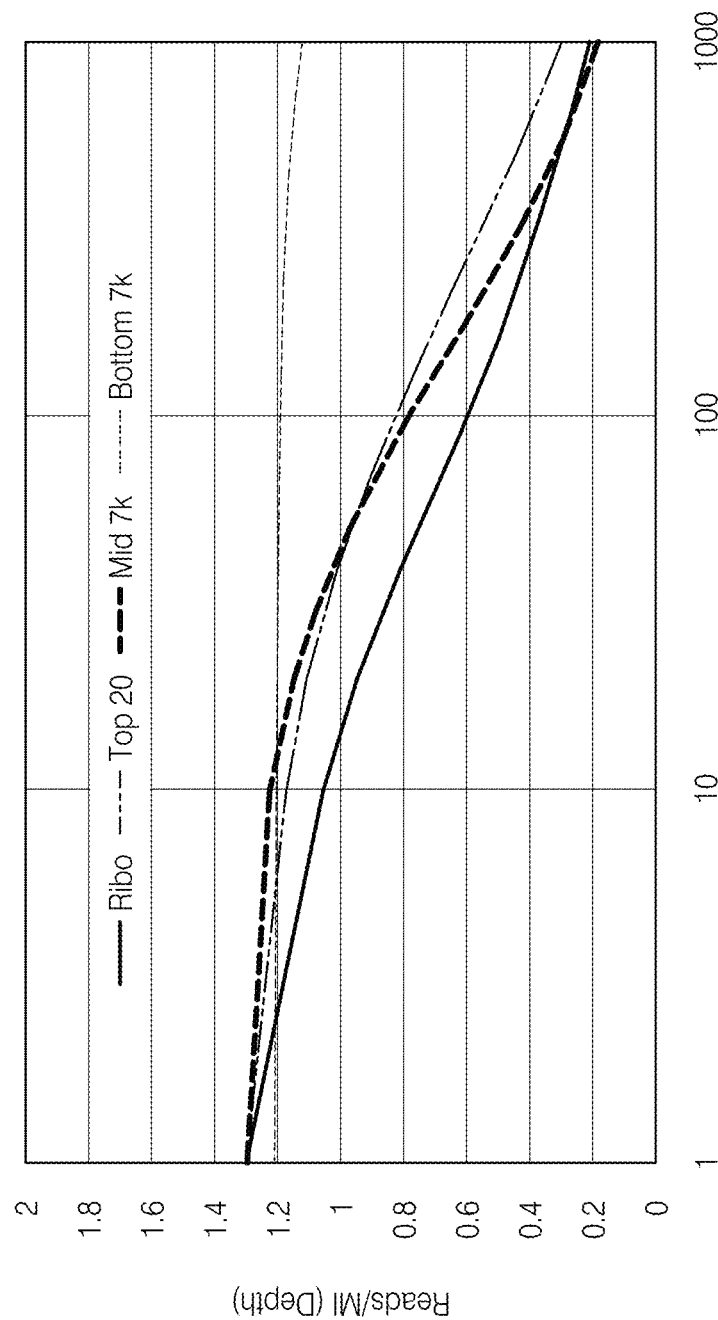
FIG. 9 shows simulated normalization results on sequencing reads per MI using shallow sequencing results from single T cell from whole transcriptome amplification data.

Example 3: Simulated from Actual T Cell Resolve WTA Data, Pretty Shallow Sequencing FIGS. 7-9 show computer simulated normalization results using actual T Cell Resolve WTA sequencing reads. Because sequencing depth for this experiment was low, this simulation cannot predict the loss of MI during normalization.

FIG. 9 shows sequencing depth changes after normalization.

Figure 10:
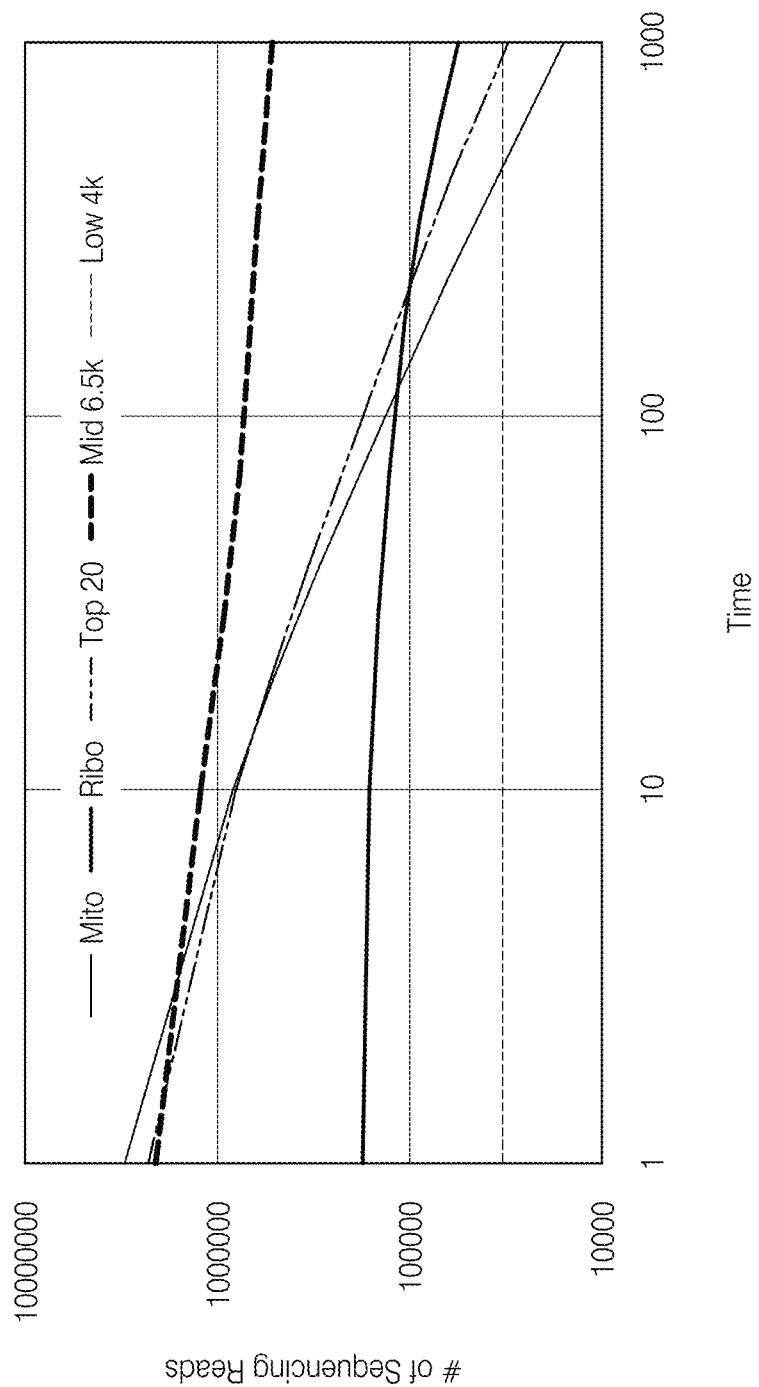
FIG. 10 shows simulated normalization results on sequencing reads using deep sequencing results from single tumor cell whole transcriptome amplification data.
Figure 11:
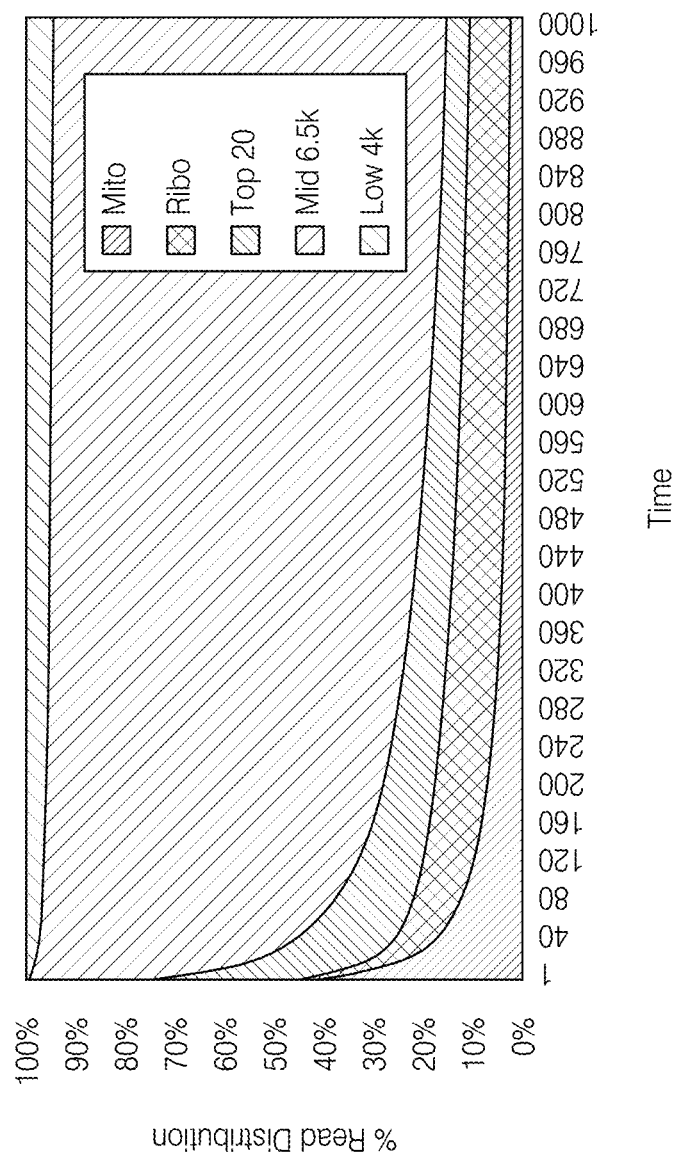
FIG. 11 shows simulated normalization results on sequencing read distribution using deep sequencing results from single tumor cell whole transcriptome amplification data.
Figure 12:
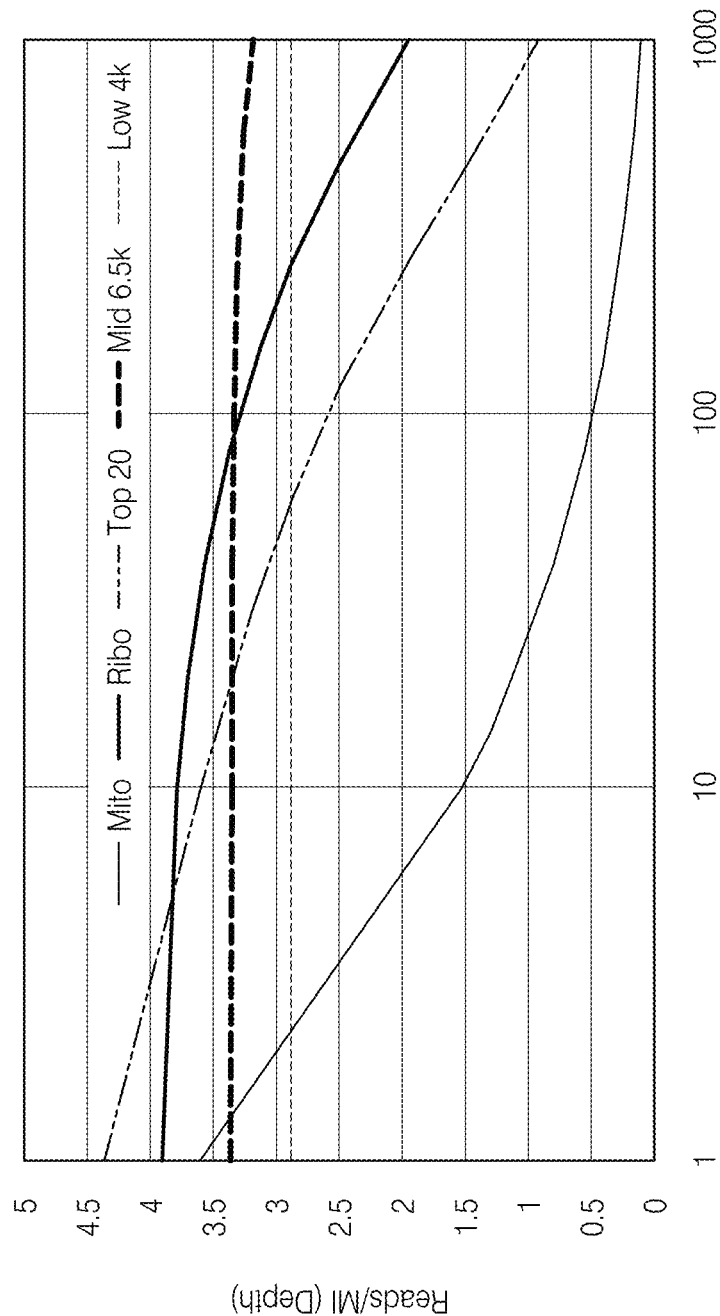
FIG. 12 shows simulated normalization results on sequencing reads per MI using deep sequencing results from single tumor cell from whole transcriptome amplification data.

Example 4: Simulated from Actual T Cell Resolve WTA Data, Next-Generation Sequencing FIGS. 10-12 show computer simulated normalization results using actual T Cell Resolve WTA data, next-generation reads. Normalization reduced mitochondrial/ribo RNA reads by 50%, increased rare transcript reads by >10-fold.

While this sequencing run is still pretty shallow, simulation shows no loss in MI counts in intermediate and low expresser genes.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of removing high abundance species from a plurality of nucleic acid molecules, comprising:
   hybridizing a plurality of first oligonucleotides comprising an affinity moiety with a first plurality of nucleic acid molecules, wherein the first plurality of nucleic acid molecules comprises at least one high abundance species, wherein the at least one high abundance species represents at least 1% of the first plurality of nucleic acid molecules;
   extending the plurality of oligonucleotides to generate a plurality of complementary strands of the first plurality of nucleic acid molecules comprising the affinity moiety;
   denaturing a plurality of double-stranded nucleic acid molecules comprising the plurality of complementary strands of the first plurality of nucleic acid molecules;

partially reannealing the plurality of complementary strands of the first plurality of nucleic acid molecules; and removing the partially reannealed complementary strands of the first plurality of nucleic acid molecules by a capture molecule immobilized on one or more solid support to generate a second plurality of nucleic acid molecules, wherein the capture molecules specifically bind to the affinity moiety, whereby the at least one high abundance species is reduced in the second plurality of nucleic acid molecules.

2. The method of claim 1, wherein the affinity moiety is a functional group selected from the group consisting of biotin, streptavidin, heparin, an aptamer, a click-chemistry moiety, digoxigenin, primary amine(s), carboxyl(s), hydroxyl(s), aldehyde(s), ketone(s), and any combination thereof.

3. The method of claim 1, further comprising synthesizing a second strand for each of the plurality of complementary strands of the first plurality of nucleic acid molecules to generate the plurality of double-stranded nucleic acid molecules comprising the plurality of complementary strands of the first plurality of nucleic acid molecules.

4. The method of claim 3, wherein the synthesizing comprises hybridizing a plurality of second oligonucleotides to the plurality of complementary strands of the first plurality of nucleic acid molecules and extending the plurality of second oligonucleotide.

5. The method of claim 4, wherein the plurality of first oligonucleotides or the plurality of second oligonucleotides comprises a universal primer binding site.

6. The method of claim 1, further comprising amplifying the plurality of double-stranded nucleic acid molecules.

7. The method of claim 1, wherein the first plurality of nucleic acid molecules comprises a plurality of high abundance species, wherein the plurality of high abundance species represents at least 10% of the first plurality of nucleic acid molecules.

8. The method of claim 7, wherein the second plurality of nucleic acid molecules comprises the plurality of high abundance species.

9. The method of claim 1, wherein the first plurality of nucleic acid molecules comprises a plurality of low abundance species, wherein a low abundance species of the plurality of low abundance species represents less than 0.1% of the first plurality of nucleic acid molecules.

10. The method of claim 9, wherein the second plurality of nucleic acid molecules comprises the plurality of low abundance species.

11. The method of claim 1, wherein each of the first plurality of nucleic acid molecules or each of the second plurality of nucleic acid molecules comprises a stochastic barcode.

12. The method of claim 1, further comprising sequencing the second plurality of nucleic acid molecules to generate a plurality of sequencing reads.

13. The method of claim 12, wherein each of the plurality of sequencing reads comprises a molecular label.

14. The method of claim 1, further comprising selectively depleting a high abundance species, wherein the high abundance species represents at least 10% of the first plurality of nucleic acid molecules.

15. The method of claim 14, wherein the selectively depleting comprises hybridizing a target-specific oligonucleotide that specifically binds to the high abundance species.

16. The method of claim 14, wherein the selectively depleting comprises treating the first plurality of nucleic acid molecules with a Cas9 protein complexed with a guide oligonucleotide that specifically binds to the high abundance species.

17. A method of generating a normalized nucleic acid library, comprising:

hybridizing a plurality of first oligonucleotides comprising an affinity moiety with a plurality of nucleic acid targets in a sample;

extending the plurality of oligonucleotides to generate a plurality of complementary strands of the plurality of nucleic acid targets comprising the affinity moiety;

denaturing a plurality of double-stranded nucleic acid molecules comprising the plurality of complementary strands of the plurality of nucleic acid targets;

partially reannealing the plurality of complementary strands of the plurality of nucleic acid targets; and removing the partially reannealed complementary strands of the plurality of nucleic acid targets by a capture molecule immobilized on one or more solid support, wherein the capture molecules specifically bind to the affinity moiety, whereby a normalized nucleic acid library of the plurality of nucleic acid targets is generated.

18. The method of claim 17, wherein the plurality of nucleic acid targets comprises mRNA.

19. The method of claim 18, wherein the plurality of nucleic acid targets comprises a plurality of low abundance species, wherein the plurality of low abundance species comprises 7,000 genes with the lowest number of transcripts within the plurality of nucleic acid targets.

20. A method of generating a normalized nucleic acid library, comprising:

hybridizing a plurality of first oligonucleotides comprising an affinity moiety with a plurality of nucleic acid targets in a sample nucleic acid library;

extending the plurality of oligonucleotides to generate a plurality of complementary strands of the plurality of nucleic acid targets comprising the affinity moiety;

denaturing a plurality of double-stranded nucleic acid molecules comprising the plurality of complementary strands of the plurality of nucleic acid targets;

partially reannealing the plurality of complementary strands of the plurality of nucleic acid targets; and removing the partially reannealed complementary strands of the plurality of nucleic acid targets, whereby a normalized nucleic acid library of the plurality of nucleic acid targets is generated.

* * * * *